US012788309B2

(12) United States Patent
Ray et al.

(10) Patent No.: US 12,788,309 B2
(45) Date of Patent: Nov. 10, 2026

(54) EPIDERMAL MICROFLUIDIC DEVICES FOR THE CAPTURE, STORAGE, AND ANALYSIS OF SWEAT

(71) Applicant: University of Hawaii, Honolulu, HI (US)

(72) Inventors: Tyler Ray, Honolulu, HI (US); Chung-Han Wu, Honolulu, HI (US); Howin Ma, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 197 days.

(21) Appl. No.: 18/689,645

(22) PCT Filed: Sep. 23, 2022

(86) PCT No.: PCT/US2022/044543
§ 371 (c)(1),
(2) Date: Mar. 6, 2024

(87) PCT Pub. No.: WO2023/049352
PCT Pub. Date: Mar. 30, 2023

(65) Prior Publication Data

US 2024/0389928 A1 Nov. 28, 2024

Related U.S. Application Data

(60) Provisional application No. 63/247,894, filed on Sep. 24, 2021.

(51) Int. Cl.
*A61B 5/00* (2006.01)
*A61B 10/00* (2006.01)
*B01L 3/00* (2006.01)

(52) U.S. Cl.
CPC .......... *A61B 5/4266* (2013.01); *A61B 5/6833* (2013.01); *A61B 10/0064* (2013.01);
(Continued)

(58) Field of Classification Search
CPC . A61B 5/4266; A61B 5/6833; A61B 10/0064; A61B 2562/164; A61B 5/14517;
(Continued)

(56) References Cited

U.S. PATENT DOCUMENTS 8,470,263 B2 6/2013 Shih et al.
9,151,701 B2 10/2015 Zhou et al.
(Continued)

FOREIGN PATENT DOCUMENTS

DE 102013101193 A1 8/2014

OTHER PUBLICATIONS

Baker, L.B., et al., "Body Map of Regional versus Whole Body Sweating Rate and Sweat Electrolyte Concentrations in Men and Women during Moderate Exercise-Heat Stress," Journal of Applied Physiology, vol. 124, Feb. 2018, 53 pages.
(Continued)

*Primary Examiner* — Andrey Shostak
(74) *Attorney, Agent, or Firm* — Withrow & Terranova, PLLC; Vincent K. Gustafson

(57) ABSTRACT

An epidermal microfluidic device includes a rigid substrate defining microfluidic features (e.g., portions of channels, valves within channels, and/or portions of reservoirs) with gradient variation in height thereof. A rigid substrate of such a devices may permit flexure during use without breakage and without distortion of microfluidic features therein, such as by providing channel-defining, reduced-width linking portions extending outward between a central portion and reservoir portions, with the reservoir portions lacking direct coupling therebetween. An epidermal interface layer comprising a flexible material and defining a first aperture may be adhered to skin of a user, and multiple microfluidic devices may be sequentially provided over, and removed from, the epidermal interface layer to collect multiple inde-
(Continued)

pendent, pristine sweat samples during an extended active collection period.

7 Claims, 18 Drawing Sheets

(52) U.S. Cl.
CPC ... *B01L 3/502738* (2013.01); *B01L 2200/027* (2013.01); *B01L 2300/0883* (2013.01); *B01L 2300/123* (2013.01); *B01L 2400/0688* (2013.01)

(58) Field of Classification Search
CPC .............. A61B 5/14546; A61B 5/6832; A61B 2562/12; B01L 3/502738; B01L 2200/027; B01L 2300/0883; B01L 2300/123; B01L 2400/0688; B01L 2200/0621; B01L 2200/0684; B01L 2300/048; B01L 2400/0406
See application file for complete search history.

(56) References Cited

U.S. PATENT DOCUMENTS

| | | | | |
|---|---|---|---|---|
| 10,925,523 | B2 | 2/2021 | Rogers et al. | |
| 2017/0156623 | A1* | 6/2017 | Chu | A61B 5/263 |
| 2018/0064377 | A1* | 3/2018 | Rogers | B01L 3/5027 |
| 2020/0088739 | A1* | 3/2020 | Rogers | A61B 5/6833 |
| 2020/0093416 | A1* | 3/2020 | Rogers | A61B 5/14546 |
| 2020/0155047 | A1* | 5/2020 | Rogers | A61B 10/0064 |
| 2020/0337641 | A1* | 10/2020 | Wang | A61B 5/145 |
| 2021/0000395 | A1 | 1/2021 | Rogers et al. | |
| 2021/0259599 | A1 | 8/2021 | Haghgooie et al. | |

OTHER PUBLICATIONS

Baker, L.B et al., "Skin-interfaced microfluidic system with personalized sweating rate and sweat chloride analytics for sports science applications," Science Advances, vol. 6, Dec. 2020, 12 pages.
Bao, Y. et al., "Recent Trends in Advanced Photoinitiators for Vat Photopolymerization 3D Printing," Macromolecular Rapid Communication, vol. 43, Issue 14, Jul. 2022, Wiley-VCH GmbH, 15 pages.
Carrell, C.S. et al., "Sealing 3D-printed parts to poly(dimethylsiloxane) for simple fabrication of Microfluidic devices," Analytica Chimica Acta, vol. 1124, Mar. 2020, Elsevier, pp. 78-84.
Choi, J. et al., "Skin-Interfaced Microfluidic Systems that Combine Hardand Soft Materials for Demanding Applications in Sweat Capture and Analysis," Advanced Healthcare Materials, vol. 10, Feb. 2021, first published Sep. 2020, Wiley-VCH GmbH, 9 pages.
Choi, J. et al., "Soft, Skin-Integrated Multifunctional Microfluidic Systems for Accurate Colorimetric Analysis of Sweat Biomarkers and Temperature," ACS Sensors, vol. 4, Feb. 2019, American Chemical Society, pp. 379-388.
Choi, J. et al., "Soft, skin-mounted microfluidic systems for measuring secretory fluidic pressures generated at the surface of the skin by eccrine sweat glands," Lab on a Chip, vol. 17, Jul. 2017, The Royal Society of Chemistry, pp. 2572-2580.
Choi, J. et al., "Thin, Soft, Skin-Mounted Microfluidic Networks with Capillary Bursting Valves for Chrono-Sampling of Sweat," Advanced Healthcare Materials, vol. 6, Issue 5, 1601355, Mar. 2017, first published Jan. 2017, Wiley-VCH, 11 pages.
Finny, A. et al., "3D Printed Hydrogel-Based Biosensors for Wearable Applications," ECS Meeting Abstracts, vol. MA2020-01, May 2020, The Electrochemical Society, 6 pages.
Ghaffari, R. et al., "Recent progress, challenges, and opportunities for wearable biochemical sensors for sweat analysis," Sensors and Actuators: B. Chemical, vol. 332, Apr. 2021, Elsevier B.V., 12 pages.
Ghaffari, R. et al., "State of Sweat: Emerging Wearable Systems for Real-Time, Noninvasive Sweat Sensing and Analytics," ACS Sensors, vol. 6, Issue 8, Aug. 2021, American Chemical Society, pp. 2787-2801.
Gong, H. et al., "Custom 3D printer and resin for 18 µm × 20 µm microfluidic flow channels," Lab on a Chip, vol. 17, Sep. 2017, The Royal Society of Chemistry, pp. 2899-2909.
Gonzalez, G. et al., "Current and emerging trends in polymeric 3D printed microfluidic devices," Additive Manufacturing, vol. 55, Jul. 2022, Elsevier B.V., 22 pages.
Katseli, V. et al., "Smartphone-Addressable 3D-Printed Electrochemical Ring for Nonenzymatic Self-Monitoring of Glucose in Human Sweat," Analytical Chemistry, vol. 93, Feb. 2021, ACS Publications, pp. 3331-3336.
Kim, T. et al., "A 3D Printed Wearable Bioelectronic Patch for Multi-Sensing and In Situ Sweat Electrolyte Monitoring," Advanced Materials Technology, vol. 6, Apr. 2021, Wiley-VCH GmbH, 11 pages.
Legrys, V.A. et al., "A multicenter evaluation of sweat chloride concentration and variation in infants with cystic fibrosis," Journal of Cystic Fibrosis, vol. 18, Mar. 2019, Elsevier B.V., pp. 190-193.
Lin, H. et al., "A programmable epidermal microfluidic valving system for wearable biofluid management and contextual biomarker analysis," Nature Communications, vol. 11, Sep. 2020, 12 pages.
Lin, H. et al., "A Wearable Electrofluidic Actuation System," Lab on a Chip, Manuscript ID: LC-COM-05-2019-000454.R1, Jul. 8, 2019, 21 pages.
Ma, B. et al., "Wearable capillary microfluidics for continuous perspiration sensing," Talanta, vol. 212, May 2020, Elsevier B.V., 6 pages.
Nielsen, A. et al., "3D Printed Microfluidics," [Author Manuscript], Annual Review of Analytical Chemistry, vol. 13, Jun. 2020, 24 pages.
Riccio, C. et al., "Effects of Curing on Photosensitive Resins in SLA Additive Manufacturing," Applied Mechanics, vol. 2, Nov. 2021, MDPI, pp. 942-955.
Stuart, T. et al., "Biosymbiotic, personalized, and digitally manufactured wireless devices for indefinite collection of high-fidelity biosignals," Science Advances, vol. 7, Oct. 2021, 18 pages.
Su, R. et al., "3D printed self-supporting elastomeric structures for multifunctional microfluidics," Science Advances, vol. 6, Oct. 2020, 10 pages.
Wu, C.-H. et al., "3D-Printed Skin-Interfaced Microfluidic Systems for Sweat Capture and Analysis," 25th International Conference on Miniaturized Systems for Chemistry and Life Sciences, Oct. 10-14, 2021, Palm Springs, CA, USA, pp. 1369-1370.
Zhang, Y. et al., "Experimental and Theoretical Studies of Serpentine Microstructures Bonded To Prestrained Elastomers for Stretchable Electronics," Advanced Functional Materials, vol. 24, Issue 14, Apr. 2014, WILEY-VCH Verlag GmbH & Co. KGaA, pp. 2028-2037.
Zhang, Y. et al., "Skin-interfaced microfluidic devices with one-opening chambers and hydrophobic valves for sweat collection and analysis," Lab on a Chip, vol. 20, Jun. 2020, The Royal Society of Chemistry, pp. 2635-2645.
International Search Report and Written Opinion for International Patent Application No. PCT/US2022/044543, mailed Feb. 14, 2023, 11 pages.

* cited by examiner

Valve 1 : 2D 90°

Valve 2 : 3D 90°

Valve 3 : Hybrid 3D 135°(top/bottom) with 90° (sides)

Valve 4 : 3D 135°

140
149a
145a
144a
141
Valve 1
147b
149b
145b
144b
147c
Valve 2
5mm
142
143
147d
144d
145d
Valve 3
149d
144c
145c
149c
147d
1245A
149a
145a

EPIDERMAL MICROFLUIDIC DEVICES FOR THE CAPTURE, STORAGE, AND ANALYSIS OF SWEAT

CROSS-REFERENCE TO RELATED APPLICATIONS

This application is a 35 U.S.C. § 371 national phase filing of International Application No. PCT/US2022/044543 filed on Sep. 23, 2022, and claims benefit of U.S. Provisional Patent Application No. 63/247,894 filed on Sep. 24, 2021, wherein the entire contents of the foregoing applications are hereby incorporated by reference herein.

GOVERNMENT RIGHTS IN INVENTION

This invention was made with government support under P20 GM113134 awarded by the National Institutes of Health. The government has certain rights in the invention.

BACKGROUND

Eccrine sweat is an attractive class of biofluid suitable for non-invasive monitoring of body chemistry. Sweat contains multiple biomarkers relevant to physiological health including electrolytes, metabolites, hormones, proteins, and exogenous agents. The intermittent or continuous assessment of these and other biomarkers in sweat may offer time-dynamic insight into metabolic processes of the body, relevant to applications ranging from athletic performance to medical diagnostics.

Traditional approaches for sweat collection employ absorbent pads or microbore tubes pressed against the epidermis by virtue of bands or straps to capture sweat as it emerges from the skin. These methods suffer from numerous limitations, such as requiring trained personnel, special handling, and costly laboratory equipment; being incompatible with real-time sweat analysis; and being prone to sample contamination or loss.

More recently, skin-interfaced microfluidic systems have been developed to offer capabilities for personalized assessment of health, nutrition, and/or wellness through non-invasive analysis of sweat. Adapting concepts from traditional lab-on-chip technologies, these wearable epidermal microfluidic (or "epifluidic") platforms may provide significant insights critical for developing personal assessments. Current device fabrication methods employ soft lithography utilizing low modulus (flexible) materials that require significant time, labor, and resource-intensive cleanroom processes to produce fluidic network designs that are restricted to planar or two-dimensional (2D) layouts. Soft lithography requires high-precision molds to form discrete, patterned layers of an elastomeric material (e.g., poly (dimethylsiloxane), PDMS) that when bonded together yield a sealed device, providing a seamless, non-irritating epidermal interface. Traditionally, producing molds with sufficient feature resolution (>20 μm) requires expensive, time-consuming processing methods (micromachining, micromilling, etc.) and access to specialized (i.e., cleanroom) environments. Such requirements result in elongated device design cycles, inequitable access to equipment necessary for innovation, and additional challenges for commercial deployment due to incompatibilities with large-scale manufacturing.

Various skin-interfaced microfluidic systems for epidermal sampling including microfluidic networks defined in flexible substrates are disclosed in U.S. Patent Application Publication No. 2021/0000395 A1 to Rogers et al. Such publication discloses microfluidic networks defined in a flexible substrate of polymeric material (e.g., polydimethylsiloxane (PDMS) among others), with the flexible substrate being used in conjunction with an adhesive layer (for adhering the device to skin) and a capping layer (for enclosing channels defined in the substrate). Each microfluidic channel defined in the flexible substrate has a fixed height, such as a channel height of 300 μm defined in a 400 μm thickness substrate. Capillary burst valves of selected burst valve pressures permit biofluid (e.g., sweat) to be supplied to different channels of a microfluidic network in a desired sequence.

The use of flexible substrates and soft lithography limits the ability to produce features of varying heights in microfluidic networks. Additionally, conventional devices have limited reservoir capacity, with limited ability to collect multiple, independent pristine samples during an extended period of active collection.

Need exists in the art for skin-interfaced microfluidic systems that address limitations associated with conventional systems.

SUMMARY

The present disclosure relates to epidermal microfluidic devices for capture, storage, and analysis of sweat. Additive manufacturing such as three-dimensional (3D) printing may be used to produce epidermal microfluidic devices using rigid materials, with features typically not obtainable using 2D fabrication methods. In certain embodiments, epidermal microfluidic devices include microfluidic features (e.g., portions of channels, valves within channels, and/or portions of reservoirs) with gradient variation in height thereof. In certain embodiments, a rigid substrate of an epidermal microfluidic device is designed to permit flexure during use without breakage and without distortion of microfluidic features therein, such as by providing channel-defining, reduced-width linking portions extending outward between a central portion and reservoir portions, with the reservoir portions lacking direct coupling therebetween. A method for collecting sweat with an epidermal microfluidic system is further provided, in which an epidermal interface layer comprising a flexible material and defining a first aperture is adhered to skin of a user. A first epidermal microfluidic device may be provided over the epidermal interface layer and used to collect sweat of the user. After reservoirs of the first epidermal microfluidic device are filled, the first epidermal microfluidic device may be removed from the epidermal interface layer, and a second epidermal microfluidic device may be provided over the same epidermal interface layer, and used to collect further sweat of the user. One or more adhesive gaskets may be provided between an epidermal interface layer and sequentially used epidermal microfluidic devices. Any suitable number of epidermal microfluidic devices may be used in sequence in conjunction with a single epidermal interface layer, to collect multiple independent, pristine samples during an extended period of active collection, wherein such devices may include rigid substrates embodying features disclosed herein.

In one aspect, the disclosure relates to an epidermal microfluidic device comprising a unitary rigid substrate and an adhesive layer. The unitary rigid substrate forms a body defining a fluid inlet port, a plurality of fluidic reservoirs, and a plurality of fluidic channels permitting fluidic communication between the fluid inlet port and the plurality of fluidic reservoirs, wherein portions of at least some of the fluidic reservoirs and/or at least some of the plurality of fluidic channels comprise gradient variations in height within the rigid substrate. The adhesive layer defines a first aperture positionally registered with the fluid inlet port, the adhesive layer being configured to be positioned between the rigid substrate and skin of a user.

In certain embodiments, the rigid substrate comprises an elastic modulus of at least 500 MPa.

In certain embodiments, the epidermal microfluidic device further comprises a reservoir capping layer arranged between the rigid substrate and the adhesive layer, wherein the reservoir capping layer comprises a second aperture positionally registered with the first aperture and the fluid inlet port.

In certain embodiments, the epidermal microfluidic device further comprises: an epidermal interface layer comprising a flexible material, configured to be positioned between the adhesive layer and the rigid substrate, and defining a third aperture; and an adhesive gasket configured to be positioned between the epidermal interface layer and the rigid substrate, and defining a fourth aperture; wherein the third aperture and the fourth aperture are positionally registered with the first aperture and the fluid inlet port.

In certain embodiments, the adhesive gasket comprises a maximum width that is smaller than a maximum width of the adhesive layer.

In certain embodiments, the body of the rigid substrate comprises a plurality of fused dots, rods, or layers.

In certain embodiments, the plurality of fluidic channels comprises one or more capillary burst valves that comprise gradient variations in height within the rigid substrate.

In certain embodiments, portions of at least some of the fluidic reservoirs comprise gradient variations in height within the rigid substrate.

In another aspect, the disclosure relates to an epidermal microfluidic device comprising a unitary rigid substrate and an adhesive layer. The unitary rigid substrate forms a body comprising a central portion, a plurality of distal portions, and a plurality of linking portions extending outward from the central portion and coupling the central portion to the plurality of distal portions, wherein the central portion defines a fluid inlet port, the plurality of distal portions define a corresponding plurality of fluidic reservoirs, and a plurality of fluid channels extend through the plurality of linking portions to provide fluid communication between the fluid inlet port and the plurality of fluidic reservoirs. Each distal portion is joined by a single corresponding linking portion to the central portion, and each linking portion has a maximum width that is less than a maximum width of each distal portion. The rigid substrate is devoid of material joining any linking portion to any other linking portion except through the central portion, and the rigid substrate is devoid of material joining any distal portion to any other distal portion except through the central portion. The adhesive layer defines a first aperture positionally registered with the fluid inlet port, the adhesive layer being configured to be positioned between the rigid substrate and skin of a user.

In certain embodiments, each linking portion of the plurality of linking portions comprises a serpentine shape.

In certain embodiments, each distal portion of the plurality of distal portions comprises a ventilation region configured to ventilate a fluidic reservoir defined in the distal portion.

In certain embodiments, the plurality of fluidic channels comprises one or more capillary burst valves.

In another aspect, the disclosure relates to a method for collecting sweat with an epidermal microfluidic system, the method comprising multiple steps. One step includes adhering an epidermal interface layer comprising a flexible material to skin of a user, the epidermal interface layer defining a first aperture. Another step includes providing a first epidermal microfluidic device over the epidermal interface layer, the first epidermal microfluidic device comprising a first body defining a first fluid inlet port, a plurality of first fluidic reservoirs, and a plurality of first fluidic channels permitting fluidic communication between the first fluid inlet port and the plurality of first fluidic reservoirs, wherein at least one adhesive gasket defining at least one gasket aperture is arranged between the first epidermal microfluidic device and the epidermal interface layer, with the first aperture and the at least one gasket aperture being positionally registered with the fluid inlet port. Another step includes collecting sweat of the user supplied through the first aperture, the at least one gasket aperture, the first fluid inlet port, and the plurality of first fluidic channels into the plurality of first fluidic reservoirs. Another step includes removing the first epidermal microfluidic device from the epidermal interface layer. Another step includes providing a second epidermal microfluidic device over the epidermal interface layer, the second epidermal microfluidic device comprising a second body defining a second fluid inlet port, a plurality of second fluidic reservoirs, and a plurality of second fluidic channels permitting fluidic communication between the second fluid inlet port and the plurality of second fluidic reservoirs, wherein at least one adhesive gasket defining a gasket aperture is arranged between the second epidermal microfluidic device and the epidermal interface layer, with the first aperture and the at least one gasket aperture being positionally registered with the second fluid inlet port. Another step includes collecting sweat of the user supplied through the first aperture, the at least one gasket aperture, the second fluid inlet port, and the plurality of second fluidic channels into the plurality of second fluidic reservoirs.

In certain embodiments, the first body is defined by a first unitary rigid substrate, in which portions of at least some of the first fluidic reservoirs and/or at least some of the plurality of first fluidic channels comprise gradient variations in height within the first unitary rigid substrate, and the second body is defined by a second unitary rigid substrate, in which portions of at least some of the second fluidic reservoirs and/or at least some of the plurality of second fluidic channels comprise gradient variations in height within the second unitary rigid substrate.

In certain embodiments, the first body is defined by a first unitary rigid substrate and comprises (i) a first central portion defining the first fluid inlet port, (ii) a plurality of distal portions defining the plurality of first fluidic reservoirs, and (iii) a plurality of first linking portions extending outward from the first central portion, defining the plurality of first fluidic channels, and coupling the first central portion to the plurality of first distal portions, wherein each first distal portion is joined by a corresponding first linking portion to the first central portion, each first linking portion has a maximum width that is less than a maximum width of each corresponding distal portion, the first unitary rigid substrate is devoid of material joining any first linking portion to any other first linking portion except through the first central portion, and the first unitary rigid substrate is devoid of material joining any first distal portion to any other first distal portion except through the first central portion; and the second body is defined by a second unitary rigid substrate and comprises (i) a second central portion defining the second fluid inlet port, (ii) a plurality of distal portions defining the plurality of second fluidic reservoirs, and (iii) a plurality of second linking portions extending outward from the second central portion, defining the plurality of second fluidic channels, and coupling the second central portion to the plurality of second distal portions, wherein each second distal portion is joined by a single corresponding second linking portion to the second central portion, each second linking portion has a maximum width that is less than a maximum width of each distal portion, the second unitary rigid substrate is devoid of material joining any second linking portion to any other second linking portion except through the second central portion, and the second unitary rigid substrate is devoid of material joining any second distal portion to any other second distal portion except through the second central portion.

In certain embodiments, each first linking portion, and each second linking portion, comprises a serpentine shape.

In certain embodiments, each of the first unitary rigid substrate and the second unitary rigid substrate comprises an elastic modulus of at least 500 MPa.

In certain embodiments, the first body of the first rigid substrate and the second body of the second rigid substrate comprises a plurality of fused dots, rods, or layers.

In certain embodiments, the plurality of first fluidic channels comprises a plurality of first capillary burst valves, and the plurality of second fluidic channels comprises a plurality of second capillary burst valves.

In another aspect, any two or more features of aspects and/or embodiments disclosed herein may be combined for additional advantage.

Additional features and advantages will be set forth in the detailed description which follows, and in part will be readily apparent to those skilled in the technical fields of microfluidic and epifluidic devices. It is to be understood that the foregoing general description, the following detailed description, and the accompanying drawings are merely exemplary and intended to provide an overview or framework to understand the nature and character of the claims.

DETAILED DESCRIPTION

Figure 1:
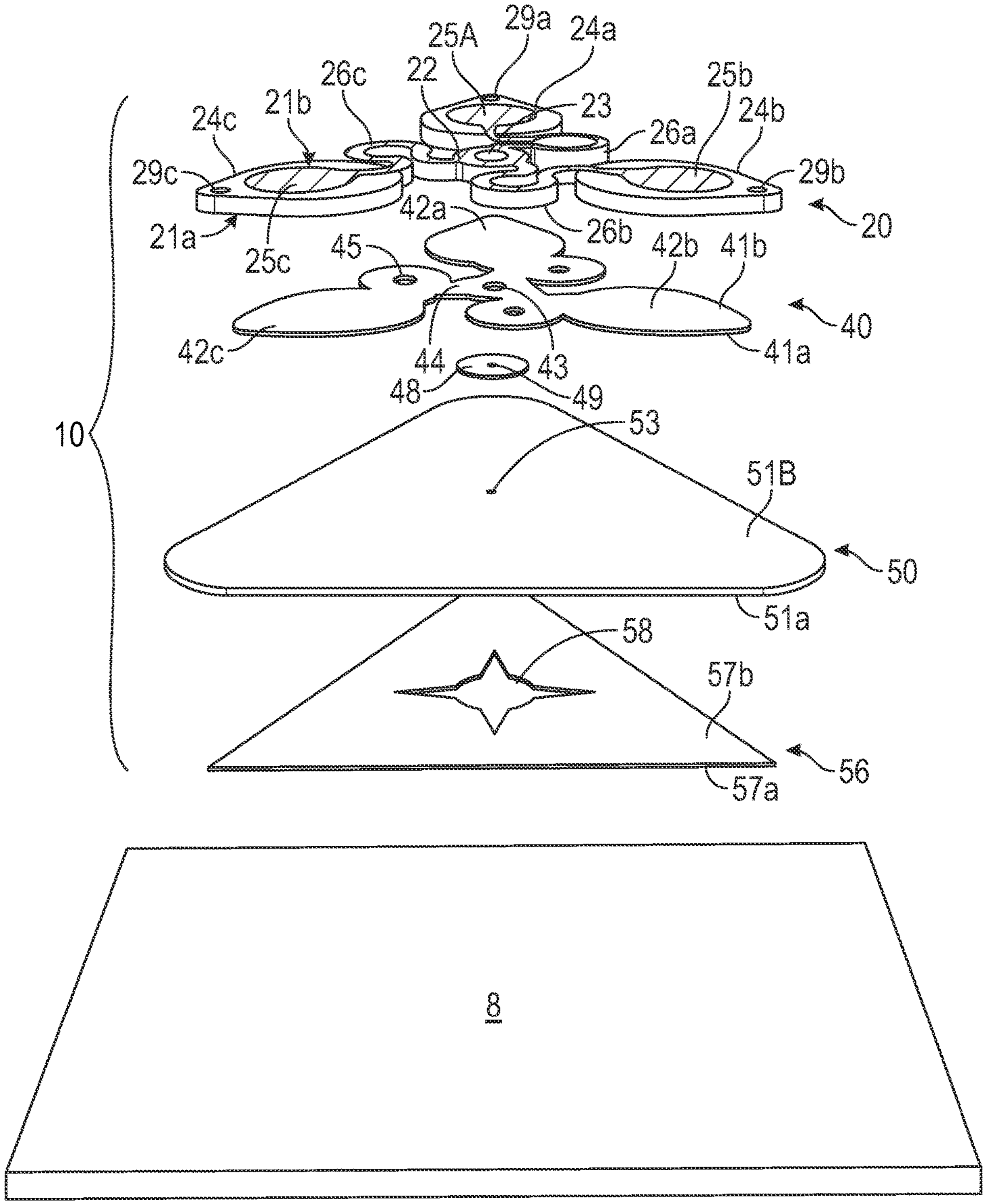
FIG. 1 is an exploded perspective view showing components of an epidermal microfluidic device including a rigid substrate, a reservoir capping layer, an adhesive gasket, an epidermal interface layer, and an adhesive layer according to one embodiment arranged over skin of a user.

Aspects of the present disclosure relate to epidermal microfluidic devices for capture, storage, and analysis of sweat. Additive manufacturing such as three-dimensional (3D) printing may be used to produce epidermal microfluidic devices using rigid materials, with microfluidic features typically not obtainable using 2D fabrication methods. Such microfluidic features with gradient variation in height may include portions of channels, capillary burst valves within channels, and/or portions of reservoirs. Rigid substrates permit features with gradient variation in height to be fabricated, and (in contrast to conventional devices fabricated of flexible materials) promote dimensional stability of microfluidic features with gradient variation in height even if a rigid substrate is subjected to flexure. In certain embodiments, a rigid substrate of an epidermal microfluidic device is designed to permit flexure during use without breakage and without distortion of microfluidic features therein, such as by providing channel-defining, reduced-width linking portions extending outward between a central portion and reservoir portions, with the reservoir portions lacking direct coupling therebetween.

In certain embodiments, a rigid substrate is produced by an additive manufacturing technique such as 3D printing. In general, these methods create solid objects in a sequential, layer-by-layer manner directly from a computer-aided design (CAD) file, typically involving deposition of liquid and/or solid materials that are cured, wherein a resulting 3D printed structure comprises a plurality of fused dots, rods, or layers. Examples of 3D printing techniques include vat photopolymerization techniques, extrusion, fused deposition modeling, direct ink writing, and the like. Although 3D printer manufacturers advertise printers with high resolution (e.g., x-y resolution of 50 microns, and z resolution of 5 microns), in practice it has historically been challenging to reliably obtain complex devices with channel dimensions of less than 100 microns that simultaneously meet various application specific requirements such as biocompatibility and/or optical clarity, while preserving printability. Careful attention to printer-dependent parameters and chemistry of printer materials improves reproducibility of high resolution microfluidic device designs capable of meeting application specific requirements.

The term "rigid substrate" as used herein refers to a substrate having an elastic modulus (a/k/a Young's modulus) value of at least 500 MPa, at least 600 MPa, at least 700 MPa, at least 800 MPa, at least 900 MPa, at least 1000 MPa, or a value within a range of from 500 to 3,000 MPa, or a value within a range of from 600 to 1,500 MPa, or a value of 700 to 1,200 MPa, or a value of about 975 MPa, in certain embodiments. In certain embodiments, a rigid substrate is produced by 3D printing and has sufficient rigidity to resist deformation of microfluidic features (e.g., channels, capillary burst valves, reservoirs, etc.) when the substrate is subjected to moderate flexural forces, but is sufficiently pliable for the substrate to resist breakage when subjected to such forces. Moreover, a rigid substrate is preferably resistive to uncontrolled fluid flow during physical handling (e.g., exertion of finger pressure).

To enhance pliability of a rigid substrate having microfluidic features defined therein, in certain embodiments a substrate may include: a central portion having a fluid inlet port, multiple distal portions each defining a corresponding fluidic reservoir, and multiple linking portions defining fluidic channels that provide fluid communication between the fluid inlet port and the multiple fluidic reservoirs, wherein each distal portion is joined by a single corresponding linking portion to the central portion, each linking portion is narrower than each distal portion (and optionally may comprise a serpentine shape), the substrate is devoid of material joining any linking portion to any other linking portion except through the central portion, and the substrate is devoid of material joining any distal portion to any other distal portion except through the central portion. Restated, providing narrow linking portions between a central portion and distal portions of a rigid substrate, without rigid substrate material (other than the central portion) coupling the respective linking portions and respective distal portions, enables the distal portions to be flexed or twisted away from a common plane to better conform to non-planar skin surfaces. The foregoing arrangement utilizes rigid substrate material only where necessary to support microfluidic structures (e.g., ports, channels, reservoirs, etc.), and permits the rigid substrate to withstand being subjected to at least moderate torsion and/or flexure without breakage, thereby permitting a rigid substrate to be used as part of an epidermal microfluidic device that conforms to non-planar skin of a user. Use of a rigid substrate instead of flexible substrate materials permits microfluidic features to remain undeformed or only minimally deformed when an epidermal microfluidic device is subjected to flexural or torsional forces, thereby eliminating concerns of unconstrained fluid flow if flexible substrate materials were employed instead.

In certain embodiments, at least some microfluidic features (e.g., reservoirs, channels, and/or capillary burst valves in channels) within a rigid substrate may comprise gradient variations in height. Although it is commonplace to provide gradient variation in width of microfluidic features, it is generally not feasible to produce gradient variation in height of microfluidic features using conventional 2D fabrication techniques. Gradient variations in height of microfluidic features within a rigid substrate may be produced by 3D printing, which may yield features having a plurality of fused dots, rods, or layers. Such features may appear to have continuous variation in height, but under a microscope may exhibit steps. Accordingly, the term "gradient variation in height" as used herein may refer to height variations produced by steps of less than 30 μm, less than 25 μm, less than 20 μm, less than 15 μm, less than 10 μm, less than 5 μm, or less than 2 μm in certain embodiments.

In certain embodiments, a fluid inlet port of a rigid substrate is configured to receive sweat of a user, where the sweat flows through at least one microfluidic channel to a series of capillary burst valves (CBVs) and corresponding reservoirs. A CBV at the ingress of each reservoir permits fluid flow only after a set pressure is exceeded, thereby enabling time-sequential sweat collection. Operating without use of actuation or moving components, capillary burst valve burst pressure is governed by valve geometry. For a microfluidic channel with fixed dimensions, the burst pressure of a CBV becomes a function of channel diverging angles, and is also inversely proportional to channel size. In certain embodiments, integrated ventilation holes are provided proximate to each reservoir to eliminate backpressure that would be generated by trapped air and impede ingress of sweat into the reservoirs.

In certain embodiments, at least one adhesive layer is provided between a rigid substrate and skin of a user, wherein the adhesive layer defines a first aperture positionally registered (i.e., aligned with) a fluid inlet port of the substrate, wherein the first aperture may be defined by laser patterning (e.g., laser ablation). The first aperture serves as a sweat collection area and may have any suitable size and shape, such as round, square, star-shaped, etc. In certain embodiments, the first aperture comprises a patterned opening that is larger than the fluid inlet port of the substrate. Although any suitable size and area of the first aperture may be selected, in certain embodiments the first aperture comprises an area in a range of 100 $mm^2$ to 400 $mm^2$, or in a range of 150 $mm^2$ to 300 $mm^2$, or in a range of about 175 $mm^2$ to about 250 $mm^2$, or a value of about 180 $mm^2$ or about 200 $mm^2$. In certain embodiments, the at least one adhesive comprises a biocompatible, medical grade adhesive layer, optionally being transparent, such as a fiber-reinforced adhesive polymeric (e.g., polyester) transfer tape material. One example of such a material is 3M Medical Transfer Adhesive 1524 (80 μm thickness) including randomly oriented polyester fibers and pressure sensitive acrylic adhesive (3M Company, St. Paul, MN, US). In certain embodiments, a single adhesive layer is provided; in other embodiments, multiple adhesive layers may be provided. In certain embodiments, one adhesive layer forms an aperture-defining gasket proximate to a central portion of a rigid substrate, and another aperture adhesive layer is larger in width and directly contacts an epidermal (skin) surface of a user, wherein an epidermal interface layer may be arranged between the foregoing two adhesive layers.

In certain embodiments, a rigid substrate comprises a skin-facing surface and a skin-opposing surface, wherein reservoir openings may be provided in the distal portions of the rigid substrate along the skin-facing surface of the rigid substrate, and the reservoir openings may be covered by a reservoir capping layer, which may be continuous or discontinuous in character. In certain embodiments, a reservoir capping layer comprises a soft material such as PDMS. In certain embodiments, a capping layer comprises a thickness in a range of from 20 μm to 50 μm, or a range of from 25 μm to 40 μm, or a thickness of about 30 μm. In certain embodiments, a reservoir capping layer may be formed directly in or on a substrate by three-dimensional printing and/or spin coating, or may be prefabricated and physically placed over at least portions of a skin-facing surface of a rigid substrate. In certain embodiments, a reservoir capping layer may be formed by pouring liquid polymer precursor (e.g., liquid PDMS with a curing agent, optionally including a pigment) onto a sacrificial film, spin coating, and curing by heat and/or other means, followed by laser cutting. Any suitable method for bonding a reservoir capping layer to a reservoir may be used, including surface modification of a rigid substrate (e.g., corona treatment with air plasma) followed by thermal bonding (e.g., lamination) between a substrate and a reservoir capping layer; chemical bonding; or adhesive bonding. In certain embodiments, a single unitary reservoir capping layer may be provided; in other embodiments, discrete (disconnected) reservoir capping layer portions may be individually provided in contact with corresponding distal portions of a rigid substrate. If a reservoir capping layer is arranged in contact (e.g., underlying) a central portion of a rigid substrate, then the reservoir capping layer may comprise a second aperture that is positionally registered (i.e., aligned) with an aperture (e.g., first aperture) of an adhesive layer as well as with the fluid inlet port of a rigid substrate.

In certain embodiments, an epidermal interface layer defining a third aperture may be provided between a skin-contacting adhesive layer and a reservoir capping layer (or between a skin-contacting adhesive layer and a rigid substrate) of an epidermal microfluidic device. In certain embodiments, an epidermal interface layer is configured to permit reversible adhesion (optionally aided by an adhesive gasket) between a skin-contacting adhesive layer and a capping layer, enabling a first rigid substrate (with associated capping layer) to be replaced, after reservoirs thereof are filled, with a second rigid substrate (and associated capping layer), thereby permitting multiple epidermal microfluidic devices (or portions thereof) to collect multiple independent pristine sweat samples during an extended period of active collection. Utilizing an epidermal interface layer provides a biocompatible fluid-tight interface with the epidermis, which provides a significant technical benefit when switching rigid substrates because it avoids adhesion challenges and potential contamination that would result in trying to adhere second and subsequent substrates to wet (i.e., sweaty) skin. In certain embodiments, an epidermal interface layer comprises PDMS or another biocompatible polymeric material, and has a thickness in a range of 200 μm to 600 μm, or in a range of 300 μm to 500 μm, or about 400 μm.

In certain embodiments, one or more functional constituents configured to interact with sweat may be arranged in or on microfluidic features of a unitary rigid substrate (e.g., supplied during fabrication, such as prior to bonding of a reservoir capping layer in certain embodiments). In certain embodiments, colorimetric assay chemicals and/or biological moieties may be arranged in or on microfluidic features of a rigid substrate to enable concentration analyses of one or more sweat constituents (e.g., chloride). In certain embodiments, dye may be arranged in or on microfluidic features of a rigid substrate to enable sweat to be visualized.

Various examples of epidermal microfluidic device designs are disclosed herein, wherein it is to be recognized that features of any one or more device designs may be combined or substituted with other device designs herein, unless indicated to the contrary.

First Exemplary Epidermal Microfluidic Device Design

FIG. 1 is an exploded perspective view of components of an epidermal microfluidic device 10 according to one embodiment arranged over skin 8 of a user. The epidermal microfluidic device 10 includes a rigid substrate 20 (including a skin-facing substrate surface 21A and a skin-opposing substrate surface 21B), a reservoir capping layer 40, an adhesive gasket 48, an epidermal interface layer 50, and an adhesive layer 56. The rigid substrate 20 forms a body including a central portion 22, three distal portions 24A-24C, and three linking portions 26A-26C that extend (laterally) outward relative to the central portion 22, wherein each linking portion 26A-26C couples a corresponding distal portion 24A-24C to the central portion 22. The central portion 22 defines a fluid inlet port 23 that is coupled to microfluidic channels (e.g., 27A-27C shown in FIG. 2) that extend through the linking portions 26A-26C to fluidic reservoirs 25A-25C defined in the distal portions 25A-25C. The fluidic reservoirs 24A-24C further include ventilation holes 29A-29C that are configured to permit escape of air from the fluidic reservoirs 25A-25C. In certain embodiments, ventilation holes 29A-29C may have a width of 100 μm and a height of 200 μm. Although FIG. 1 shows the fluidic reservoirs 25A-25C with hatching, this is intended to depict fluid (e.g., sweat, optionally colored with a dye) therein, wherein such fluid may be visible when the rigid substrate 20 (or at least the skin-opposing substrate surface 21B) comprises a transparent or at least partially light-transmissive material.

With continued reference to FIG. 1, a reservoir capping layer 40 (e.g., fabricated of a soft material such as PDMS, optionally including pigment of white or another color) including central portion 43 defining a first aperture 43, and including three projecting portions 42A-42C, is positioned below the rigid substrate 20, with a skin-opposing capping layer surface 41B facing the rigid substrate 20, and with a skin-facing capping layer surface 41A facing the underlying epidermal interface layer 50. The first aperture 43 is positionally aligned with the overlying fluidic inlet port 23 of the rigid substrate 20 and a gasket aperture 49 defined in an underlying adhesive gasket 48. The reservoir capping layer 40 also includes three secondary openings 45 that are positioned below recurved areas of linking portions 26A-26C of the rigid substrate 20. An epidermal interface layer 50 is positioned below both the adhesive gasket 48 and the reservoir capping layer 40, with a skin-opposing interface layer surface 51B facing the reservoir capping layer 40, and with a skin-facing interface layer surface 51A facing an underlying adhesive layer 56. The epidermal interface layer 50, which may be larger in length and width than the rigid substrate 20, defines an aperture 53 that is positionally aligned with the overlying gasket aperture 49 and the adhesive layer aperture 58 defined in the underlying adhesive layer 56. The adhesive layer 56 has a skin-facing adhesive layer surface 57A and a skin-opposing adhesive layer surface 57B, and defines an adhesive layer aperture 58 that serves as a sweat collection area. As shown, the adhesive layer aperture 58 is fashioned in a four-pointed star shape and is aligned with (but larger than) each of the overlying apertures 53, 49, 43 and the fluid inlet port 23. The adhesive layer 56 is configured to contact skin 8 of a user and the overlying epidermal interface layer 50.

Figure 2:
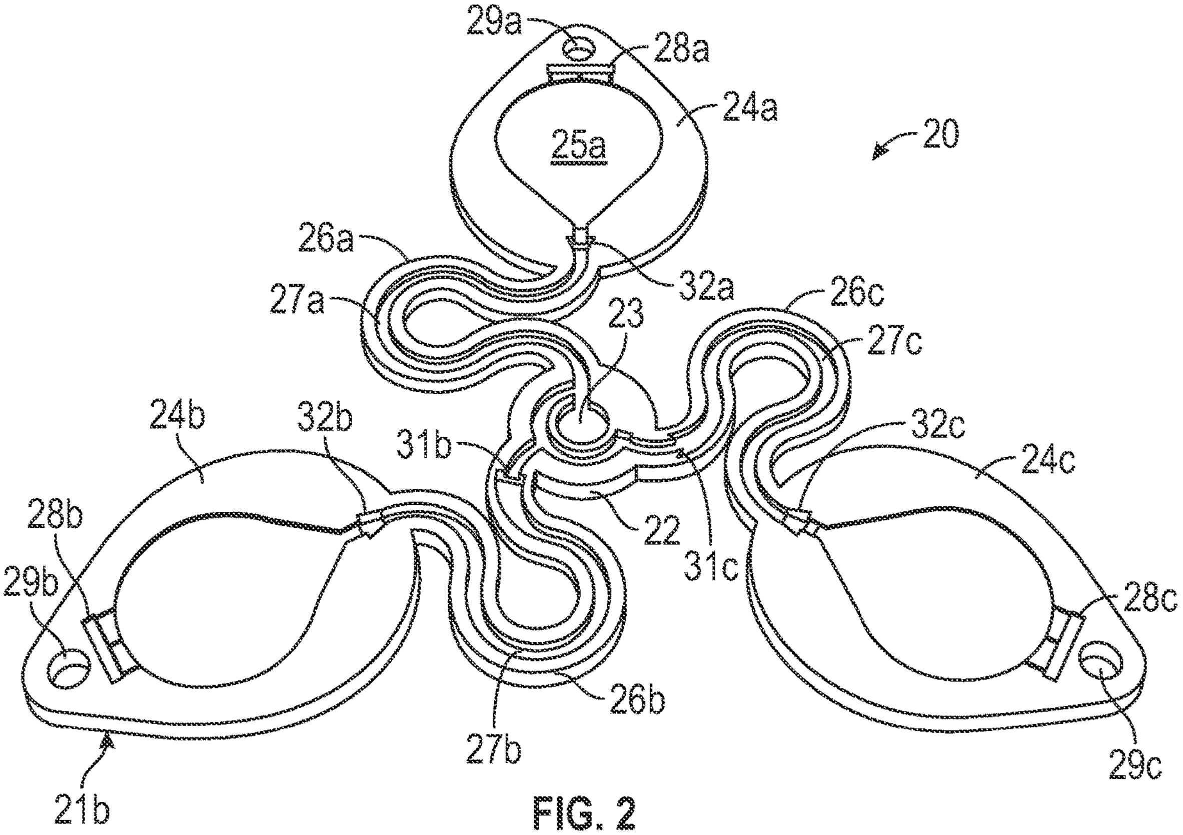
FIG. 2 is a perspective view of a horizontally sectioned upper portion of a unitary rigid substrate of the epidermal microfluidic device of FIG. 1, including a body comprising a central portion, a plurality of distal portions, and a plurality of linking portions extending outward from the central portion and coupling the central portion to the distal portions, with fluid channels defined in the central portion providing fluid communication with fluidic reservoirs defined in the distal portions.

FIG. 2 is a perspective view of a horizontally sectioned upper portion of the rigid substrate 20 of FIG. 1, showing internal details thereof. The first to third linking portions 26A-26C define first to third microfluidic channels 27A-27C, respectively, extending from the fluid inlet port 23 to the reservoirs 25A-25C defined in the distal portions 24A-24C. The first microfluidic channel 27A is devoid of any upstream capillary burst valve (CBV) proximate to the fluidic inlet 23, but includes a first downstream CBV 32A at the inlet to the first reservoir 25A. The second and third microfluidic channels 27B, 27C include respective second and third upstream CBVs 31B, 31C proximate to the fluidic inlet 23, and include respective second and third downstream CBVs 32B, 32C proximate to the second and third reservoirs 25B, 25C. At least some of the CBVs 31B-31C, 32A-32C and/or at least portions of the reservoirs 25A-25C comprise gradient variations in height thereof. The various CBVs differ in burst pressure to cause fluid (i.e., sweat) to enter and fill the reservoirs 25A-25C in sequential order. For example, sweat entering the rigid substrate 20 through the fluidic inlet port 23 will initially fill the first microfluidic channel 27 and upon attainment of the burst pressure of the first downstream CBV 32A, will enter the first fluidic reservoir 25A. Additionally, gas permeation members 28A-28C (which may comprise liquid impermeable but gas permeable membranes or other capillary structures) are arranged in the distal portions 24A-24C between the fluidic reservoirs 25A-25C and the corresponding ventilation holes 29A-29C in the distal portions 24A-24C, wherein the ventilation holes 29A-29C allow escape of air displaced by movement of fluid into the corresponding fluidic reservoirs 25A-25C.

Figure 3:
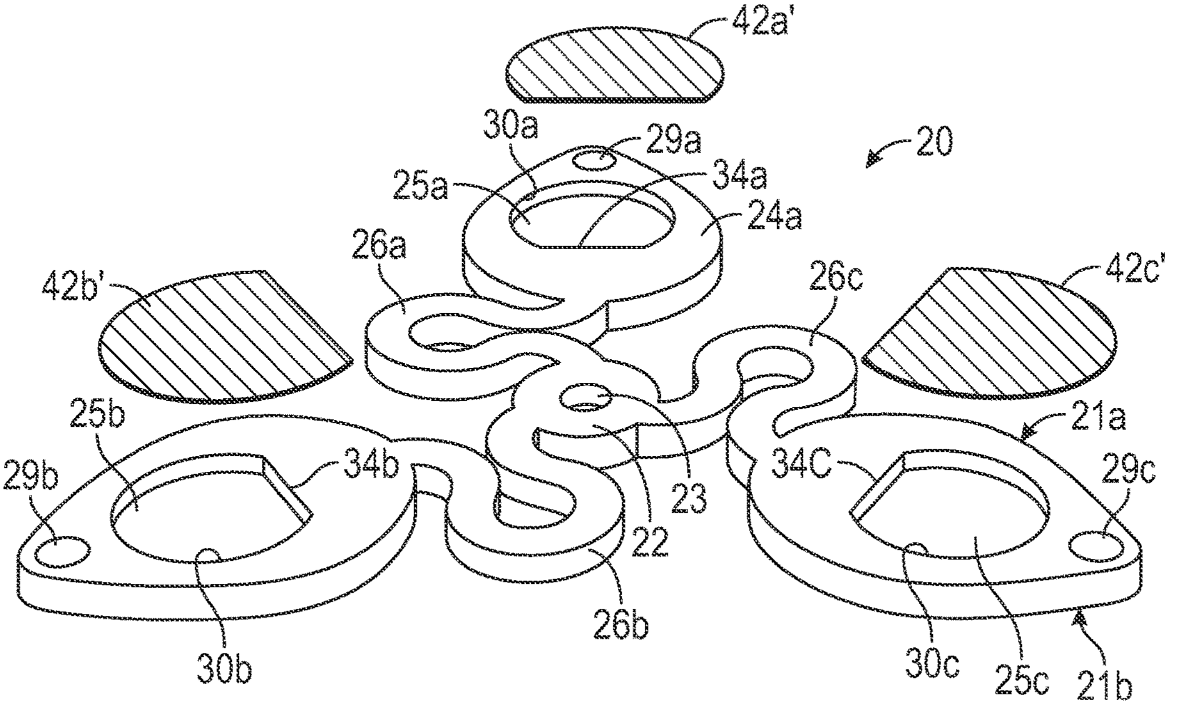
FIG. 3 is a perspective view of the unitary rigid substrate of the epidermal microfluidic device of FIG. 1, with superimposed capping layer portions arranged over fluidic reservoirs defined in distal portions of the substrate.

FIG. 3 is a perspective view of the unitary rigid substrate 20 of FIG. 1, oriented upside-down, showing reservoir openings 30A-30C in the skin-facing substrate surface 21A into the fluidic reservoirs 25A-25C, with superimposed reservoir capping layer portions 42A'-42C' arranged over the reservoir openings 30A-30C. As shown, each fluidic reservoir 25A-25C has a straight transverse edge 34A-34C not appearing in FIG. 1, with the straight transverse edge 34A-34C representing a boundary of a gradient thickness portion of the skin-facing substrate surface 21A, such that a portion of each fluidic reservoir 25A-25C has a gradient variation in height thereof. The remainder of the skin-facing substrate surface 21A (except for the fluidic inlet port 23 and the ventilation holes 29A-29C) is continuous and uninterrupted across the central portion 22, the linking portions 26A-26C, and the distal portions 25A-25C. The discontinuous reservoir capping layer portions 42A'-42C' are provided as an alternative to the single continuous reservoir capping layer 40 shown in FIG. 1.

Figure 4:
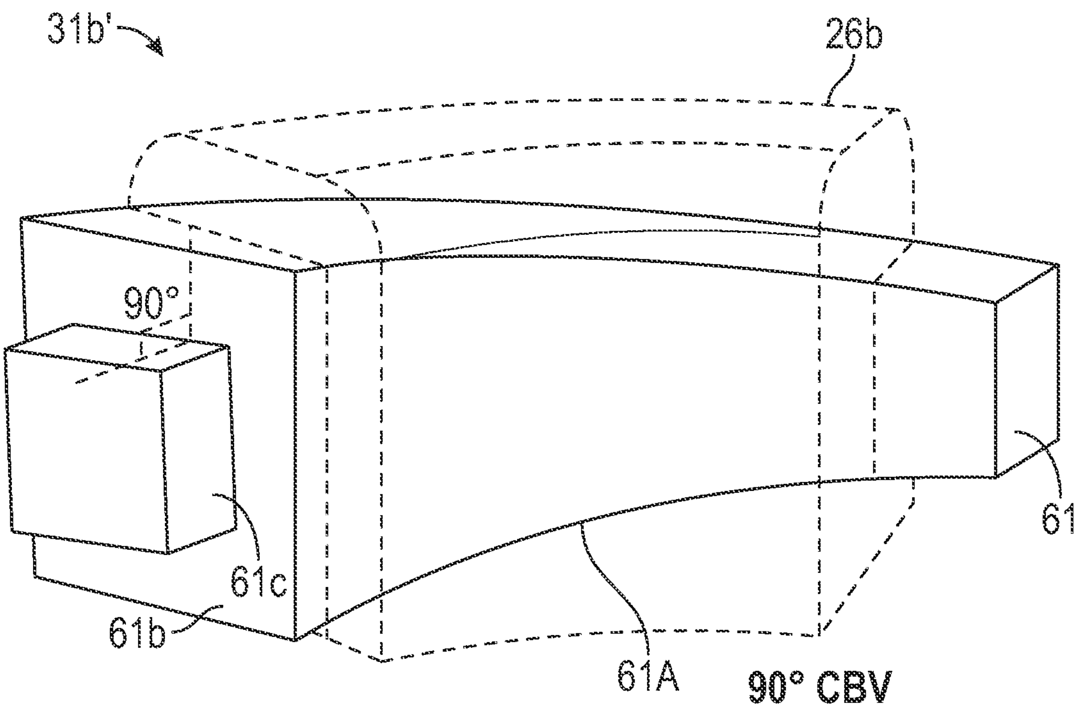
FIG. 4 is a perspective view illustration of fluid occupying a first capillary burst valve (CBV) having a diverging angle of 90 degrees and having microfluidic channel portion of continuously varying height and width, with the CBV and channel portion being useable within a rigid substrate of an epidermal microfluidic device according to one embodiment.

FIG. 4 is a perspective view illustration of fluid 61 occupying a first CBV 31B' (corresponding in shape to the second upstream CBV shown in FIG. 2) defined in a second linking portion 26B. A first portion of fluid 61A occupies a microfluidic channel portion of continuously varying height and width (including gradient variation in height), a second portion of fluid 61B exerts pressure against a width reducing barrier wall (not shown), and a third portion of fluid 61C flows into a reduced width channel section (not shown). A diverging angle of 90 degrees between the first and second fluid portions 61A, 61B (as defined by the solid structures surrounding the fluid portions) extends in both width and height dimensions, such that a three dimensional 90 degree CBV is formed.

Figure 5:
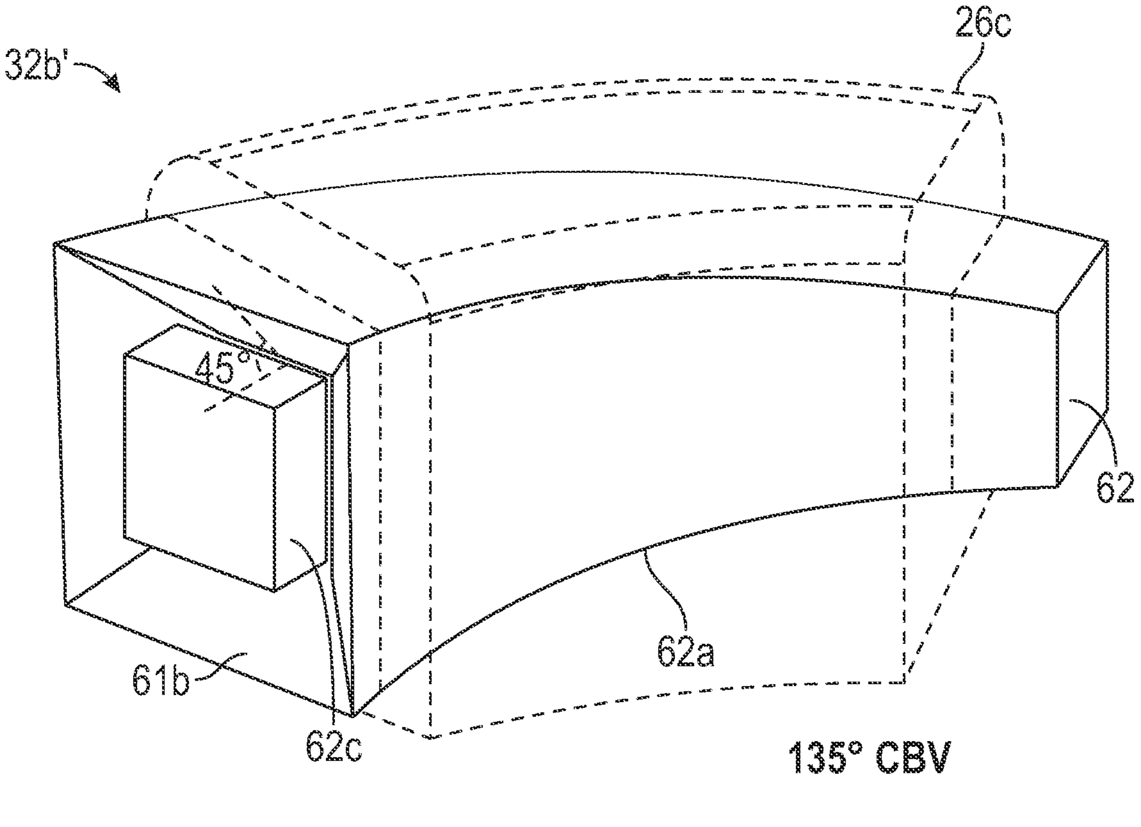
FIG. 5 is a perspective view illustration of fluid occupying a second capillary burst valve (CBV) having a diverging angle of 135 degrees and having a microfluidic channel portion of continuously varying height and width, with the CBV and channel portion being useable within a rigid substrate of an epidermal microfluidic device according to one embodiment.

FIG. 5 is a perspective view illustration of fluid 62 occupying a second CBV 32C' (corresponding in shape to the third downstream CBV shown in FIG. 2) defined in a third linking portion 26C. A first portion of fluid 62A occupies a microfluidic channel portion of continuously varying height and width (including gradient variation in height), a second portion of fluid 62B exerts pressure against a width reducing barrier wall (not shown), and a third portion of fluid 62C flows into a reduced width channel section (not shown). A diverging angle of 135 degrees (embodying the complementary angle to the illustrated 45°, extending into the linking portion 26C) between the first and second fluid portions 62A, 62B (as defined by the solid structures surrounding the fluid portions) extends in both width and height dimension to form a three dimensional 135 degree CBV.

Figure 6:
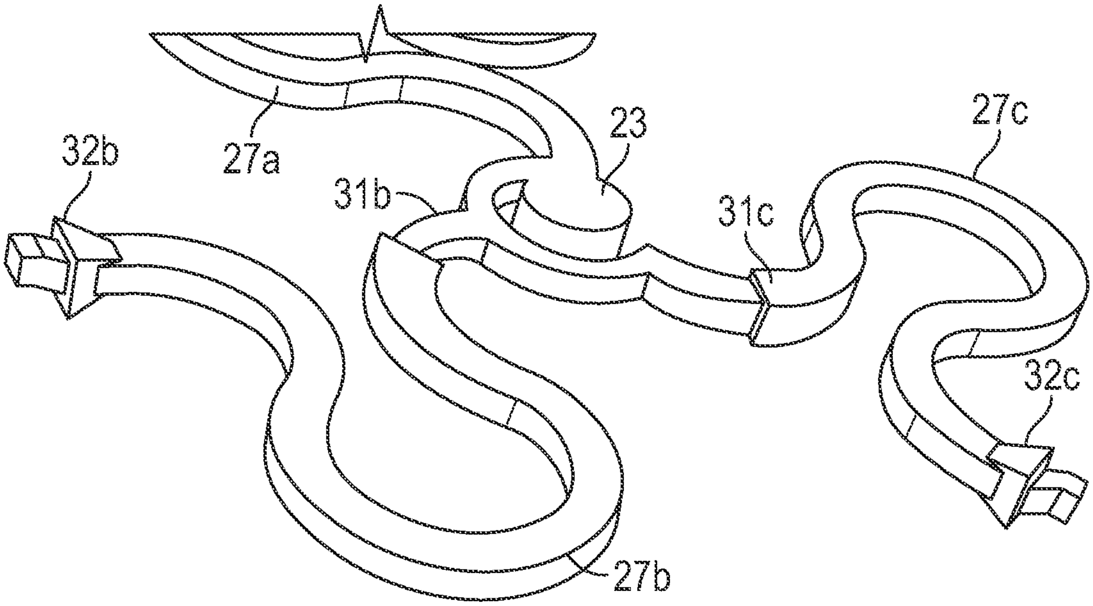
FIG. 6 is a perspective view illustration of fluid within internal channels and selected CBVs of a portion of the rigid substrate of FIGS. 1-3.

FIG. 6 is a perspective view illustration of fluid within internal channels 27A-27C and selected CBVs 31B-31C, 32B-32C of a portion of the rigid substrate 20 of FIGS. 1-3.

Such figure shows that the internal channel 27C proximate to the upstream CBV 31C exhibits stepwise variations in height and width, but the internal channels 27B, 27C exhibit gradient variations in height and width proximate to the CBVs 31B, 32B, 32C.

Figure 7:
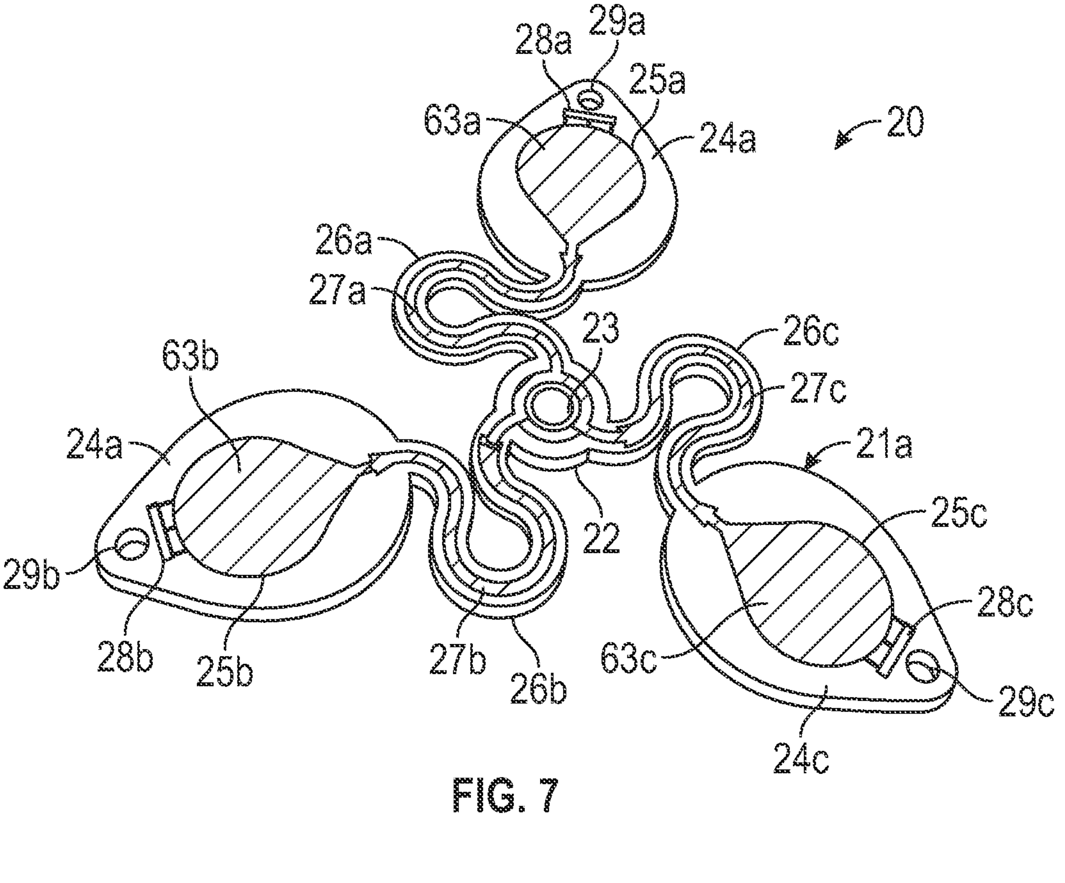
FIG. 7 is a lower perspective view of the unitary rigid substrate of the epidermal microfluidic device of FIG. 1, showing fluid within channels and reservoirs thereof, visible through a light transmissive surface.

FIG. 7 is a lower perspective view of the unitary rigid substrate 20 of FIG. 1, showing fluid portions 63A-63C within channels 27A-27C and reservoirs 25A-25C thereof, visible through a light transmissive skin-facing substrate surface 21A. The remaining items of FIG. 7 are the same as previously described in FIGS. 1-3 and need not be described again.

Figure 8A:
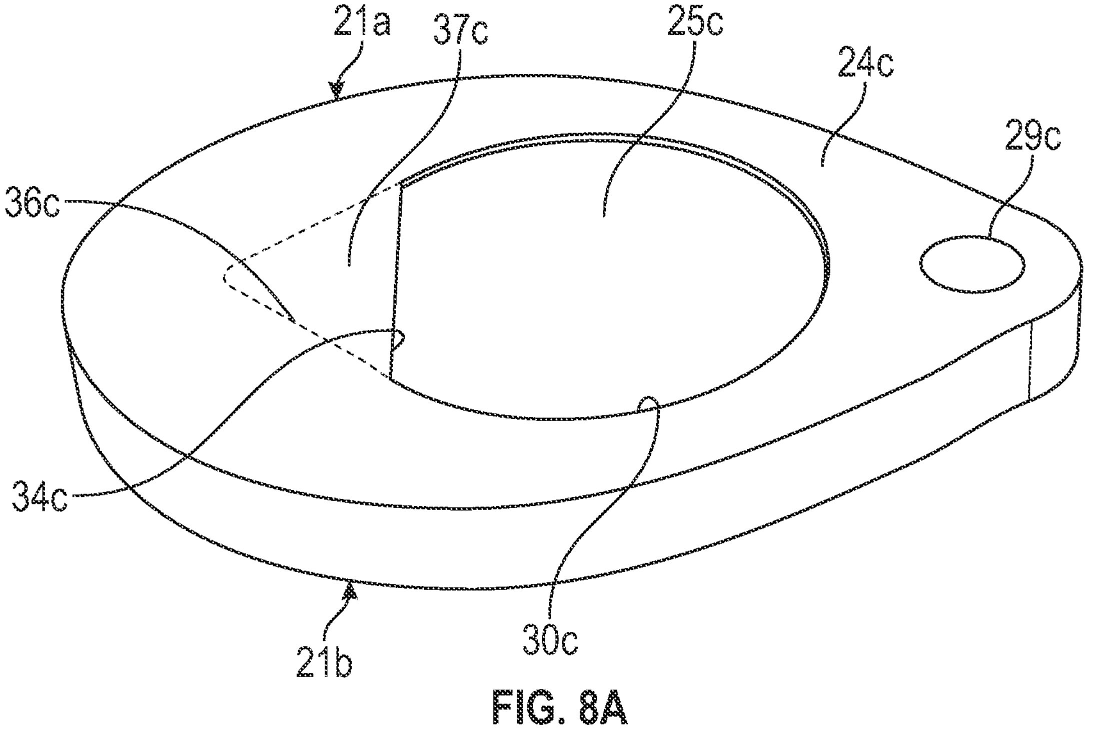
FIG. 8A is a lower perspective view of a distal portion of the epidermal microfluidic device of FIG. 3, with superimposed dashed lines showing sidewalls of a reservoir therein.

FIG. 8A is a lower perspective view of a distal portion 24C of the epidermal microfluidic device of FIG. 3, with superimposed dashed lines showing sidewalls 36C of a fluidic reservoir 25C that are hidden by a gradient thickness portion 37C of the skin-facing substrate surface 21A bounding a portion of the fluidic reservoir 25C. The gradient thickness portion 37C is bounded by a straight transverse edge 34C that represents a minimum (non-zero) thickness of the gradient thickness portion, with the straight transverse edge bounding a portion of the reservoir opening 30C defined in the skin-facing substrate wall 21A, wherein the reservoir opening 30C may be covered by a reservoir capping layer (e.g., 42 in FIG. 1 or 42C' in FIG. 3). The gradient thickness portion 37C causes a portion of the fluidic reservoir 25C to have a gradient variation in height, which may aid in predictably uniform filling of the fluidic reservoir 25C as a fluid front advances within the fluidic reservoir 25C due to both sweat-driven pressure (i.e., flow driven by natural pressures created by sweat glands) and capillary action.

Figure 8B:
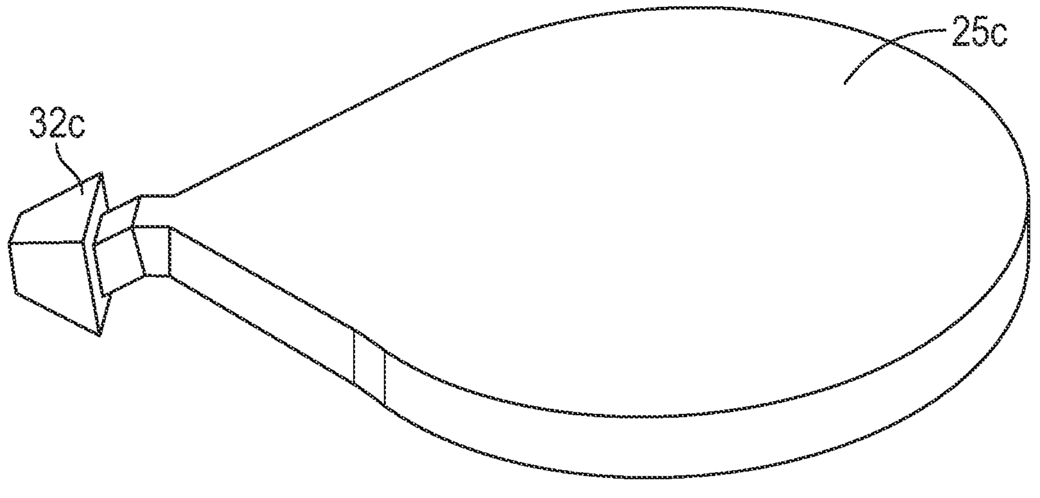
FIG. 8B is a perspective view illustration of fluid within the fluidic reservoir and a capillary burst valve of the distal portion of the epidermal microfluidic device of FIG. 8A.

FIG. 8B is a perspective view illustration of fluid within the fluidic reservoir 25C and a capillary burst valve (CBV) 32C internal to the distal portion 24C of FIG. 8A. As shown, both the CBV 32C and portions of the fluidic reservoir 25C exhibit gradient variations in height (and width).

Figure 8C:
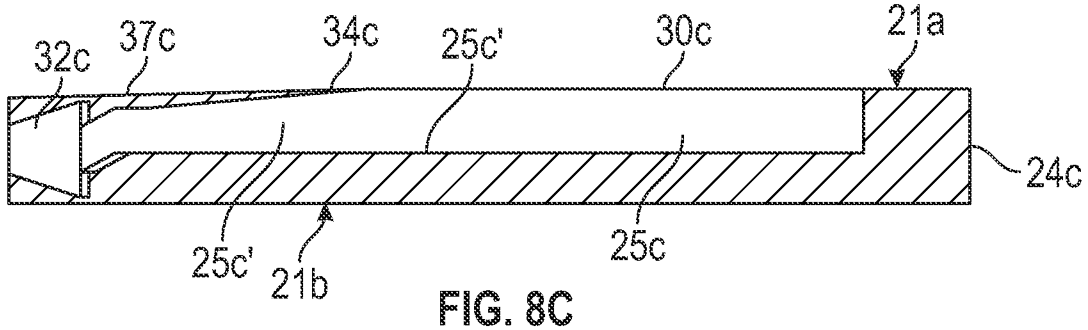
FIG. 8C is a side cross-sectional view of the distal portion of the epidermal microfluidic device of FIG. 8A, showing continuous variation in thickness of portions of a reservoir therein.

FIG. 8C is a side cross-sectional view of the distal portion 24C of FIG. 8A, showing continuous variation in thickness of the CBV 32C and portions of the fluidic reservoir 25C therein. In particular, the gradient thickness portion 37C of the skin-facing substrate surface 21A (with the gradient thickness portion 37C terminating at the straight transverse edge 34C that bounds a portion of the reservoir opening 30C) causes a portion of the fluidic reservoir 25C to have a gradient variation in height between the CBV 32C and the reservoir opening 30C, wherein the fluidic reservoir 25C is bounded a face wall 25C' having a substantially constant thickness along the skin-opposing surface 21B.

Figure 9A:
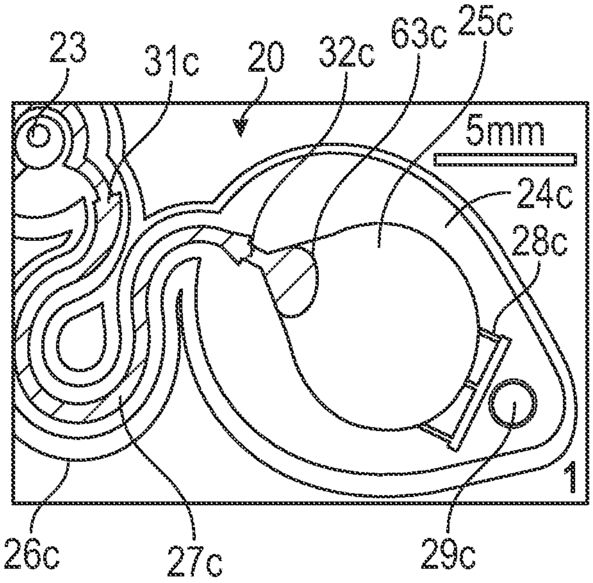
FIGS. 9A-9D are top plan views of a portion of an epidermal microfluidic device according to one embodiment, showing a reservoir in four different states of being filled with liquid.
Figure 9B:
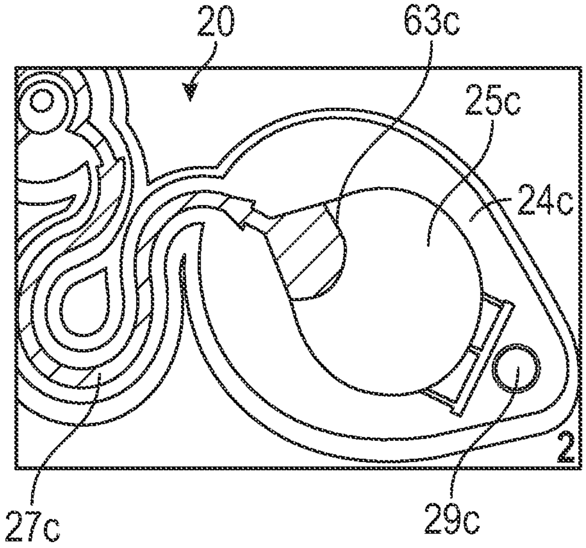
Figure 9C:
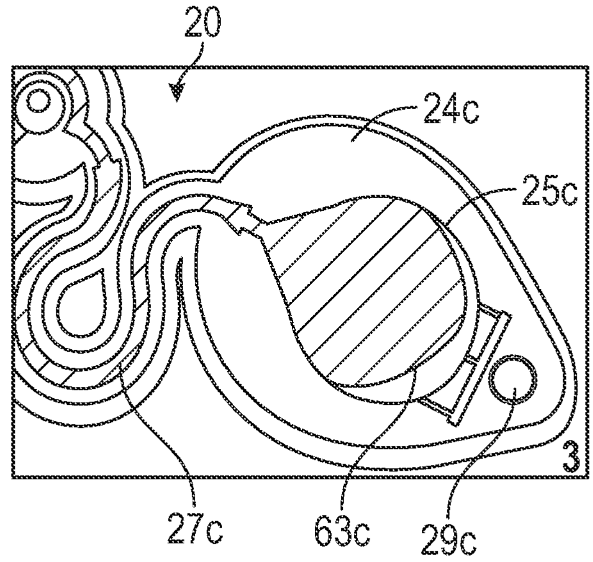
Figure 9D:
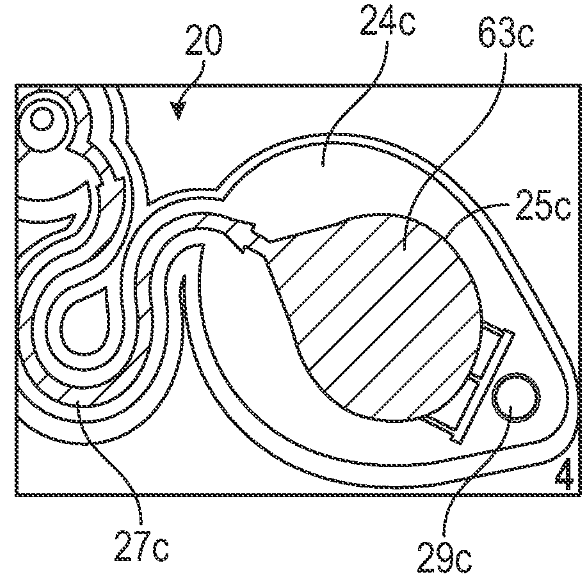

FIGS. 9A-9D are top plan views of a portion of an epidermal microfluidic device 20 according to FIG. 7, showing a fluidic reservoir 25 (defined in distal portion 24C) in four different states of being filled with fluid (e.g., sweat). In FIG. 9A, a fluid front supplied through inlet port 23 (defined in central portion 22) has already moved through upstream CBV 31, through channel 27C (defined in linking portion 26C), and through downstream CBV 32C to provide an advancing fluid front 63C within the fluidic reservoir 25C, as air within the fluidic reservoir 25C is displaced through gas permeation member 28C and ventilation hole 29C. In FIGS. 9B and 9C, the advancing fluid front 63C has filled consecutively larger portions of the fluidic reservoir 25C, until the entire fluidic reservoir 25C is filled in FIG. 9D. Providing gradient variation in height of the fluidic reservoir 25C (e.g., as shown in FIG. 8C) causes the fluid front 63C to advance in a predictable bulk manner within the fluidic reservoir 25C (e.g., instead of along edges of the fluidic reservoir 25C), which may aid in visual determination of filling state of the fluidic reservoir 25C.

Design and Printing Considerations for Improved 3D Device Fabrication

Successful fabrication of a fully-enclosed microfluidic channel with feature sizes at the x-y plane resolution limit of current DLP printers (~30 μm to 50 μm) depends on several related factors including: design aspects (e.g., channel vertical position), print process parameters (e.g., layer height, layer cure time (LCT), print speed), and printer hardware (e.g., projector light power, wavelength). Optimization of user-adjustable factors results in a robust print process suitable for producing microfluidic devices with sufficient optical clarity, dimensional fidelity, and mechanical performance for use in epidermal microfluidic applications.

Figure 10A:
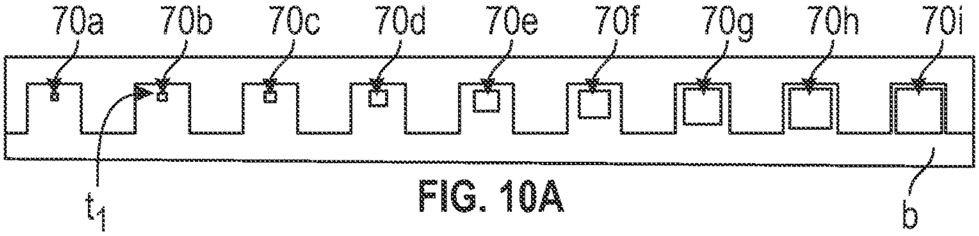
FIG. 10A provides cross-sectional views of nine 3D-printed test channels of substantially square cross sectional shapes ranging in dimensions from 100 μm to 900 μm.

As expected, epidermal microfluidic device performance is dependent on the dimensional accuracy of a 3D fabrication process. If not quantified, unintended deviation from designed dimensions can adversely affect component performance (e.g., CBV burst pressure) or measurement accuracy (e.g., sweat volume, sweat rate, etc.). To evaluate dimensional accuracy of a 3D fabrication process, nine test channels of substantially square cross-sectional shapes ranging in dimensions from 100 μm to 900 μm (in both width and height) and 5 mm long were fabricated by 3D printing, to permit determination of the minimum repeatable printable channel dimensions and sidewall thickness (minimum 50 μm). FIG. 10A provides cross-sectional views of the nine 3D-printed test channels 70A-70I with height and width dimensions from 100 μm to 900 μm (i.e., ranging from 100 μm by 100 μm for test channel 70A to 900 μm by 900 μm for test channel 70I). The asymmetric vertical position of the channels 70A-70I establishes a uniform capping layer (100 μm) thickness $t_1$ across all channel dimensions tested. Since the selected digital light process (DLP)-based printer produces structures in an inverse manner (i.e., the base b prints first), the position of the channels 70A-70I minimized photopolymerizing resin trapped in the channels 70A-70I during the 3D printing process.

Figure 10B:
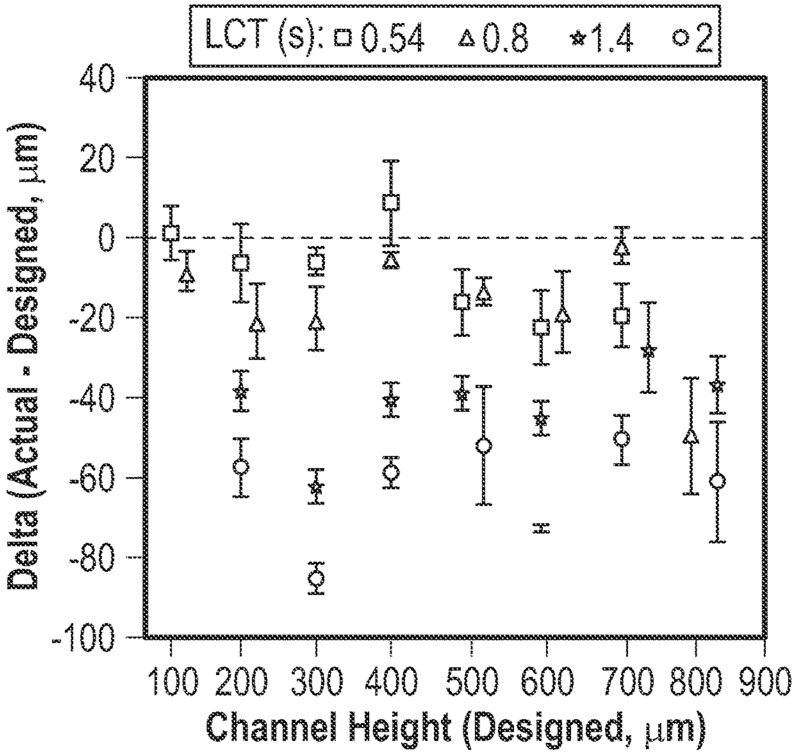
FIG. 10B is a plot of variation in 3D printed channel height from designed dimensions for nine different channel heights and four different layer cure time (LCT) values.
Figure 10C:
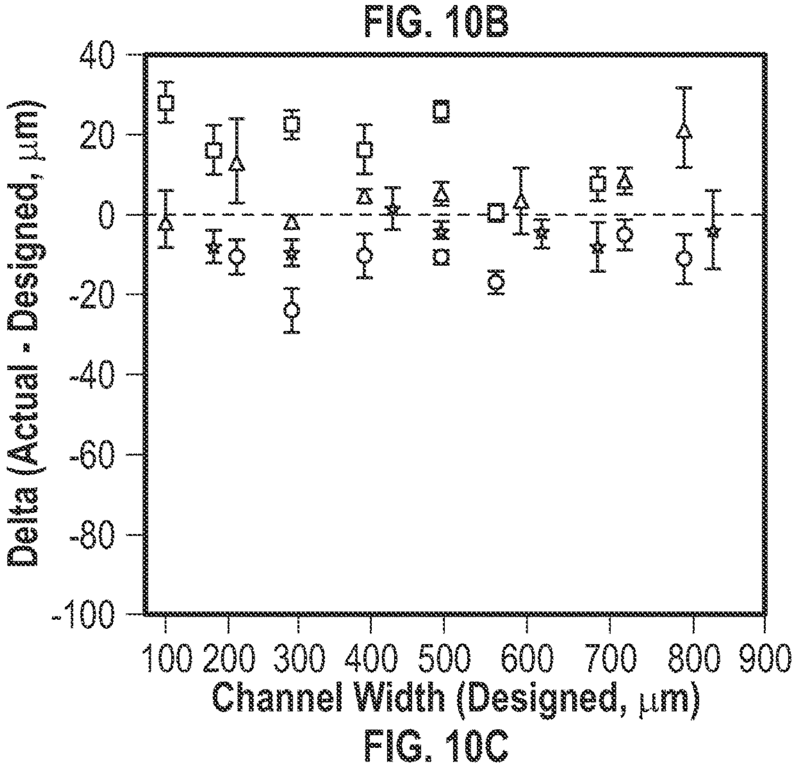
FIG. 10C is a plot of variation in 3D printed channel width from designed dimensions for nine different channel widths and four different layer cure time (LCT) values.

Experimental studies also have revealed a strong influence of layer cure time (LCT) on 3D print success using a DLP-based 3D printer and resulting quality of DLP 3D printed substrates of epidermal microfluidic devices. The LCT defines the energy dose used to crosslink a photopolymer used in DLP-based 3D printing, given in time (seconds). The projector wavelength is defined by hardware (e.g., 385 nm in production of the test channels 70A-70I). Systematic studies of four LCT settings (i.e., 0.54 s, 0.8 s, 1.4 s, 2 s, from tested minimum (0.54 s) to maximum values (2.0 s)(0.6 s interval) beyond which channels could not be fabricated successfully) establish a relationship between 3D print performance (i.e., for successful channel printing), dimensional accuracy, and optical clarity. Measurement results obtained from optical microscope are plotted in FIG. 10B for channel height and in FIG. 10C for channel width, and highlight the relationship between LCT and printed channel dimensions. Referring to FIG. 10B, the proportional relationship between increasing LCT and light propagation into the z-dimension (thickness) of the masked regions (i.e., channels) results in smaller-than-designed channel heights. By comparison, and referring to FIG. 10C, the dimensional accuracy for a given channel width depends primarily on the size of DLP printer pixels (x-y plane resolution) rather than LCT. The observed positive channel width variation with decreasing LCT indicates incomplete photopolymerization. Subsequent post-processing removal of uncured resin yields channels with dimensions greater than designed. In combination, these results establish the printable region for an epidermal microfluidic design as a function of LCT. As shown in FIGS. 10B and 10C, successful fabrication of a 100 μm square channel (i.e., channel 70A in FIG. 10A) requires a short LCT (i.e., 0.54 s, 0.8 s) whereas a longer LCT results in photopolymerization of the otherwise unreacted resin. Conversely, for large dimensions (greater than 700 μm square, corresponding to channels 70G to 70I in FIG. 10A), a short LCT produces channels too fragile to survive printing and post-processing due to incomplete photopolymerization. These results establish an LCT of 0.8 s as the optimal setting for balancing printability with dimensional accuracy for the printed substrates of epidermal microfluidic devices using the selected DLP printing apparatus. Other settings may be appropriate for producing 3D printed epidermal microfluidic device substrates using different printing equipment.

Additional systematic experiments establish the DLP-printable design space for dimensions relevant to epidermal microfluidic devices (e.g., 100 μm-600 μm). An encapsulated microfluidic channel capable of supporting unrestricted fluid flow, in contrast to a sealed or partially-restricted channel, defines a successful print. Intuitively, print failure rate increases as the enclosed channel dimensions approach the printer x-y plane resolution limit (e.g., ~32 μm square pixel for the selected DLP-based printer). Experimental results showed that channel dimensions of 100 μm (either width or height) correspond to the lower limit for a successful printed device.

Print Process Optimization for Colorimetric Analysis in 3D Printed Systems

The optical transparency of a 3D-printed microfluidic device depends on several factors including material selection, printer hardware (e.g., build plate, vat surface material), post processing, and surface roughness. In contrast to the typical surface roughness feature size necessary for optical transparency (<10 nm), DLP printers produce parts with microscale surface roughness resulting in a semi-translucent appearance.

As mentioned previously, pixel size of a digital micromirror device (DMD) governs the x-y plane resolution of a DLP 3D printer. Minute gaps between individual DMD elements locally reduce reflected light intensity, yielding a surface roughness with features corresponding to DMD pixel size and layer height. Although specialized printing methods (e.g., grayscale) or printer hardware (e.g., oscillating lenses) offer sophisticated strategies to reduce aliasing and improve surface roughness, the fundamental approach to eliminating this defect mode is enhancing the uniformity of projected light to ensure complete photopolymerization. UV-Vis spectroscopy experiments examined the transmission properties of 3D-printed microcuvettes produced by such method in comparison to a commercial plastic cuvette. In particular, a UV-Vis spectrophotometer (UV-1900i, Shimadzu, Japan) enabled quantification of the optical transmission properties of the 3D printed devices (300 nm-1000 nm, 0.5 nm interval). A commercial plastic cuvette (10 mm pathlength, Shimadzu) served as a reference (control). Four (4) sets of 3D-printed cuvettes (N=3 per set) utilizing a different LCT setting (0.54 s, 0.8 s, 1.4 s, 2 s) enable quantification of the relationship between LCT and optical transmission (external dimensions: 50 mm height, 8 mm width, 1 mm pathlength, ~21 μL volume). The inventors have found that increasing the exposure dose by lengthening the LCT eliminated the observed grid pattern defects (from DMD element gaps) and improved optical transparency.

Figure 11:
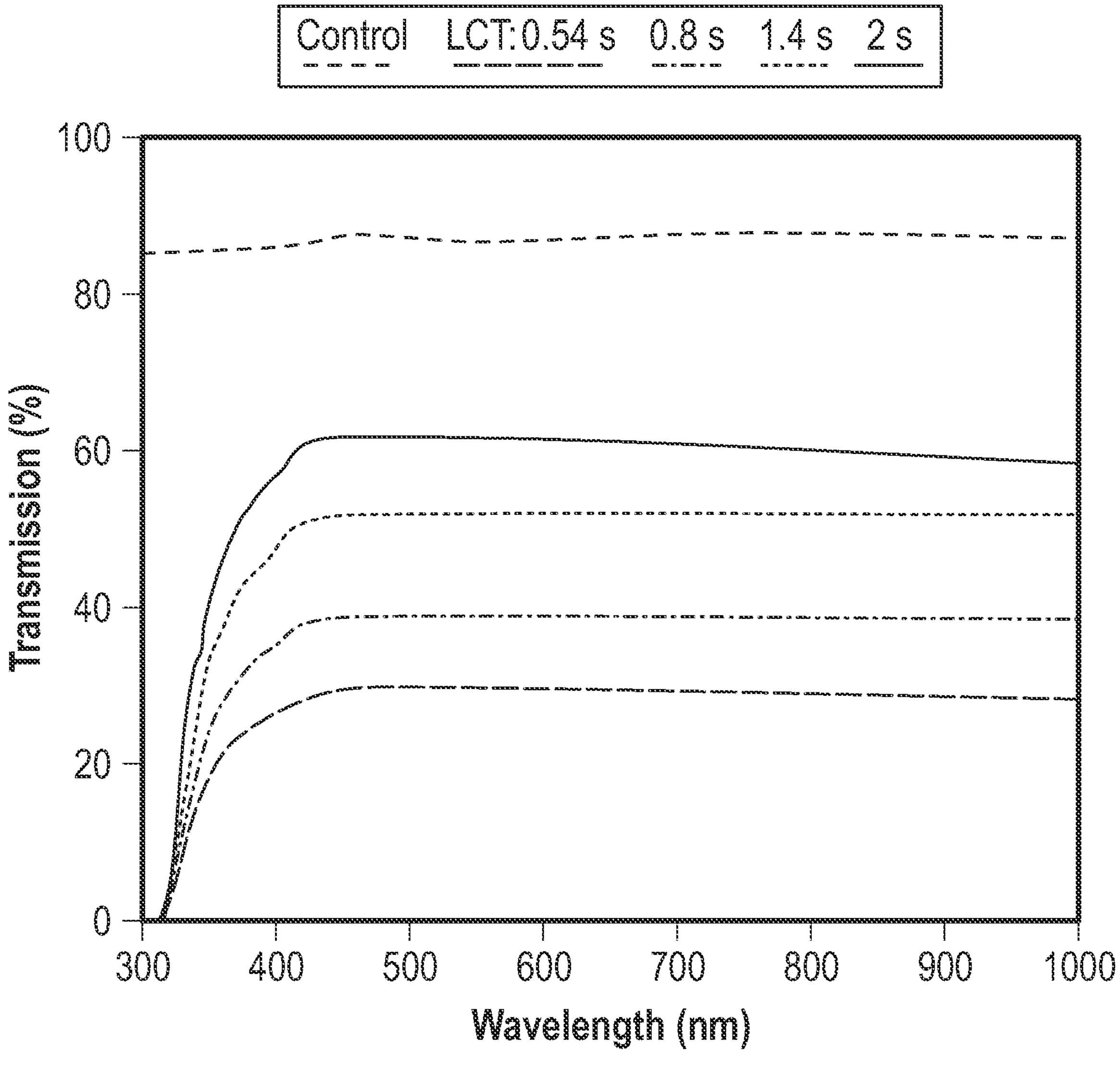
FIG. 11 is a plot of light transmission percentage versus wavelength for 3D-printed microcuvettes at four different layer cure time (LCT) values in comparison to a commercial plastic cuvette.

FIG. 11 is a plot of light transmission percentage versus wavelength for 3D-printed microcuvettes at four different layer cure time (LCT) values in comparison to a commercial plastic cuvette. While FIG. 11 shows significant modulation of light transmission with increasing LCT, ranging from ~20% (LCT 0.54 s) to ~60% (LCT 2 s), the reference commercial plastic cuvette offers higher light transmission (~80%). Intuitively, there is no observed wavelength dependence for light transmission within the visible spectrum (400 nm-1000 nm) beyond the anticipated strong absorbance within the UV region (<400 nm, necessary for photopolymerization) for the 3D-printed samples. As a consequence of the presence of both the UV absorber and photoinitiator in the resin, green parts (i.e. uncured) possess a light yellow hue. Appropriate selection and use of post processing may further reduce or eliminate coloring of 3D printed microfluidic substrates.

In addition to LCT, layer height affects both overall device quality (e.g., vertical resolution, optical clarity, channel roughness) and print time, which corresponds to device yield. Conventional approaches to vat photopolymerization utilize constant values for a given print run (i.e. fixed layer height, LCT). At present, only one manufacturer (i.e., Formlabs) supports an adaptive layer height process to increase print speed by adjusting layer height as a function of model detail (i.e., small layers for fine features, thick layers for coarse features). Adaptive printing is an attractive process for obtaining expanded design flexibility for 3D-printed epidermal microfluidic systems. Although not supported by default, a combination of custom software and manual G-code (geometric code) programming enables definition of both layer height and LCT as a function of model dimensions. By comparison to a constant LCT and layer height setting printing process, this approach enables successful, time-efficient fabrication of epidermal microfluidic devices with complex geometries and high device quality.

Colorimetric assays facilitate passive, battery-free in situ quantitative measurement of sweat biomarkers. A chemical reagent reacts with a target species to generate an optical signal proportional to analyte concentration. Accurate colorimetric analysis requires channels with uniform height (i.e., path length), a high degree of optical transparency, and integrated color reference markers to support reliable image processing under variable ambient lighting conditions. The layer-by-layer control over LCT and layer height parameters during printing enabled by an adaptive printing process is highly desirable for fabricating microfluidic devices with the requisite surface finish and optical transparency to support colorimetric analysis. The inventors have found that an adaptive LCT print process beneficially improves optical transparency of microfluidic features in 3D printed substrates, wherein optical clarity for two representative epidermal microfluidic device reservoirs manufactured utilizing a layer-constant LCT (0.54 s, 2 s) was found to increase with longer LCT. While beneficial for reducing nonuniform illumination, the increased UV dose results in undesirable curing of resin in enclosed features (channels, CBVs). By comparison, an adaptive printing process (AP1) utilizing an LCT of 0.54 s for the reservoir surface and an LCT of 2 s for subsequent layers enables fabrication of microfluidic substrate with a translucent imaging plane, transparent faces, and preservation of internal channel features. An inverse adaptive printing process (AP2; base LCT: 2 s, subsequent layer LCT: 0.54 s) results in an optically transparent imaging plane and a translucent device.

Systematic benchtop experiments evaluate the suitability of devices fabricated by adaptive printing for colorimetric analysis. The colorimetric assay silver chloranilate produces a dark violet color response proportional to chloride concentration. Imaging the device with a smartphone camera enables color extraction and subsequent quantification of color response. The inclusion of a color balance chart facilitates color calibration for each image. As previously reported by others, converting images from native red-green-blue (RGB) color space to CIELAB color space (which expresses color as lightness (L), amount of green to red (a*), and amount of yellow to blue (b*)) ensures device-independent color sampling. Conversion of the a* and b* components to chroma (C*) by the relation $$C^* = (a^{*2} + b^{*2})^{1/2} \quad \text{[Equation 1]}$$

yields a calibration curve (with chloride concentration by a power-law relation). Calibration charts were created from 3D-printed epidermal microfluidic device substrates with different LCT parameters and reference colorimetric assay solutions, revealing that the improvement in optical clarity with increasing LCT provides a corresponding enhancement in the range of detectable color measurements. Thus, an adaptive printing process is helpful for fabricating epidermal microfluidic device substrates with an optical transparency sufficient to support colorimetric analysis.

Capillary Burst Valve Designs and Additional Epifluidic Devices

CBVs are a key component for the sequential analysis of sweat biomarkers in many epifluidic platforms. Time-dynamic variations in sweat rate arising from physical (e.g., sweat gland density), physiological (e.g., exertion, emotion), and external factors (e.g., temperature, pH) result in corresponding changes in analyte concentration. As previously described, CBVs prevent flow for fluid pressure conditions below a designed threshold (bursting pressure, BP); when the fluid pressure exceeds the BP, the CBV immediately bursts. Operating without use of actuation or moving components, CBV BP is governed by valve geometry.

The Young-Laplace equation describes the BP for a CBV (rectangular channel) as $$BP = -2\sigma\left[\frac{\cos\theta_I^*}{b} + \frac{\cos\theta_A}{h}\right] \quad \text{[Equation 2]}$$

where σ is the fluid surface tension; $\theta_A$+ is the critical advancing contact angle for the channel (material dependent, $\theta_A$=120° for PDMS); $\theta_I$* is the minimum of either θ+β or 180°; β is the (horizontal) channel diverging angle; b and h are the diverging channel width and height, respectively. As the second term of Equation 2 is constant for a planar (i.e., two-dimensional or 2D) CBV, channel width and diverging angle govern the BP for a given CBV. In practice, epidermal microfluidic device designs utilize geometric restrictions (i.e., modifications to channel width) to control valve BP.

Figure 12A:
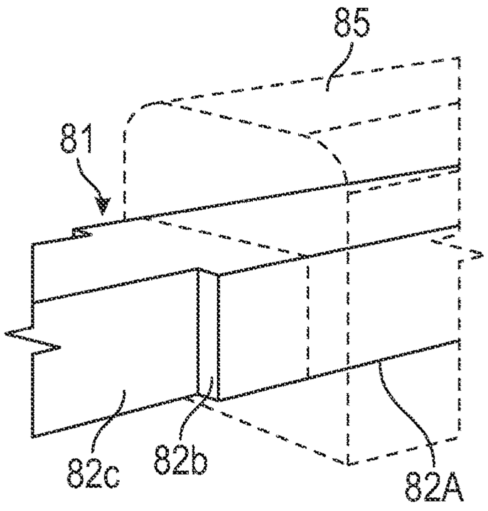
FIGS. 12A-12D illustrate fluid occupying first to fourth different capillary burst valves, respectively.
Figure 12B:
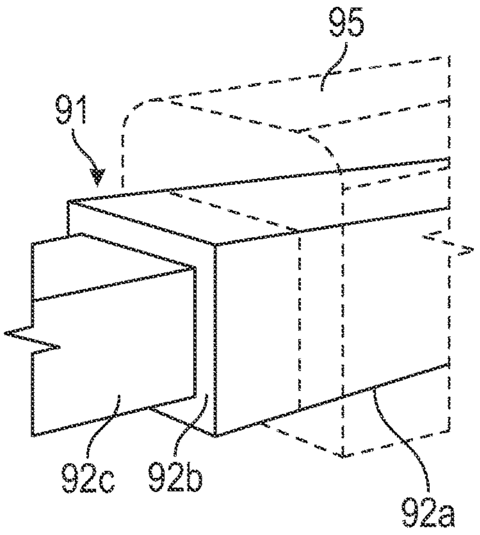
Figure 12C:
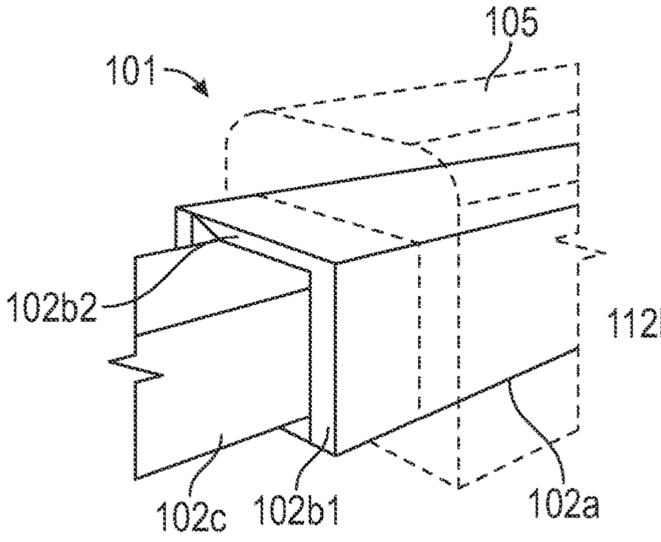
Figure 12D:
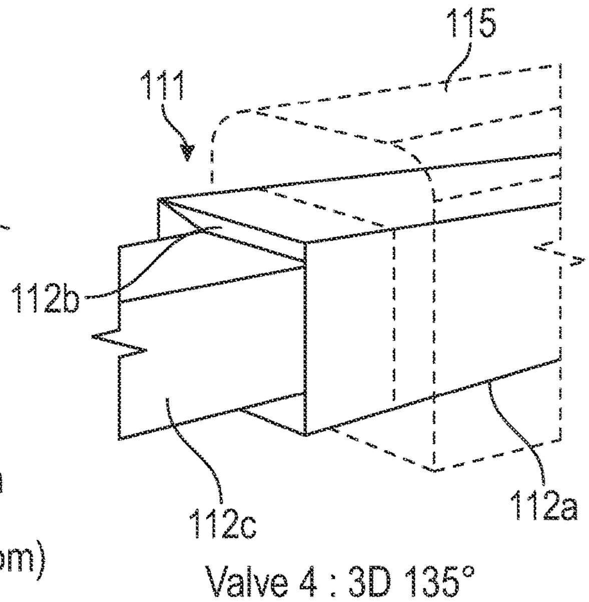

Utilization of 3D printing to produce substrates of epidermal microfluidic devices as disclosed herein expands CBV capabilities by enabling full 3D CBV designs. As a consequence, for a 3D CBV, Equation 2 can be written as $$BP = -2\sigma\left[\frac{\cos\theta_I^*}{b} + \frac{\cos\theta_J^*}{h}\right] \quad \text{[Equation 3]}$$

where $\theta^*_J$ is the minimum of either θ+γ or 180° and γ is the channel diverging angle (z-axis). It follows that for a microfluidic channel with fixed dimensions, the CBV BP becomes a function of the channel diverging angles (β, γ). Computational predictions of four representative CBV valve designs, presented schematically in FIGS. 12A-12D, with parameters specified in Table 1 hereinafter, illustrate this relationship. FIG. 12A illustrates fluid occupying a first CBV 81 defined in a linking portion 85 (or other part of a 3D printed substrate), wherein a first fluid portion 82A is arranged upstream of the first CBV 81, a second fluid portion 82B exerts pressure against a width reducing barrier wall (not shown), and a third fluid portion 82C flows into a reduced width channel portion (not shown). A horizontal diverging angle of 90 degrees is provided between the first and second fluid portions 82A, 82B, forming a 2D 90 degree CBV. FIG. 12B illustrates fluid occupying a second CBV 91 defined in a linking portion 95, wherein a first fluid portion 92A is arranged upstream of the second CBV 91, a second fluid portion 92B exerts pressure against a height- and width-reducing barrier wall (not shown), and a third fluid portion 92C flows into a reduced width channel portion (not shown). Horizontal and vertical diverging angles of 90 degrees are provided between the first and second fluid portions 92A, 92B, forming a 3D 90 degree CBV. FIG. 12C illustrates fluid occupying a third CBV 101 defined in a linking portion 105, wherein a first fluid portion 102A is arranged upstream of the third CBV 101, second fluid portions 102B1, 102B2 exert pressure against width- and height-reducing barrier walls (not shown), and a third fluid portion 102C flows into a reduced width channel portion (not shown). A horizontal diverging angle of 90 degrees and a vertical diverging angle of 135 degrees are provided between the first and second fluid portions 102A, 102B, forming a hybrid 135 degree (vertical)/90 degree (horizontal) CBV. FIG. 12D illustrates fluid occupying a fourth CBV 111 defined in a linking portion 115, wherein a first fluid portion 112A is arranged upstream of the fourth CBV 111, a second fluid portion 112B exerts pressure against a height- and width-reducing barrier wall (not shown), and a third fluid portion 112C flows into a reduced width channel portion (not shown). Horizontal and vertical diverging angles of 135 degrees are provided between the first and second fluid portions 112A, 112B, forming a 3D 135 degree CBV.

TABLE 1

Diverging angle parameters for each CBV type.

| CBV Type | Geometry | β | γ |
|---|---|---|---|
| 1 | 2D | 90° | N/A |
| 2 | 3D | 90° | 90° |
| 3 | 3D | 90° | 135° |
| 4 | 3D | 135° | 135° |

Figure 13A:
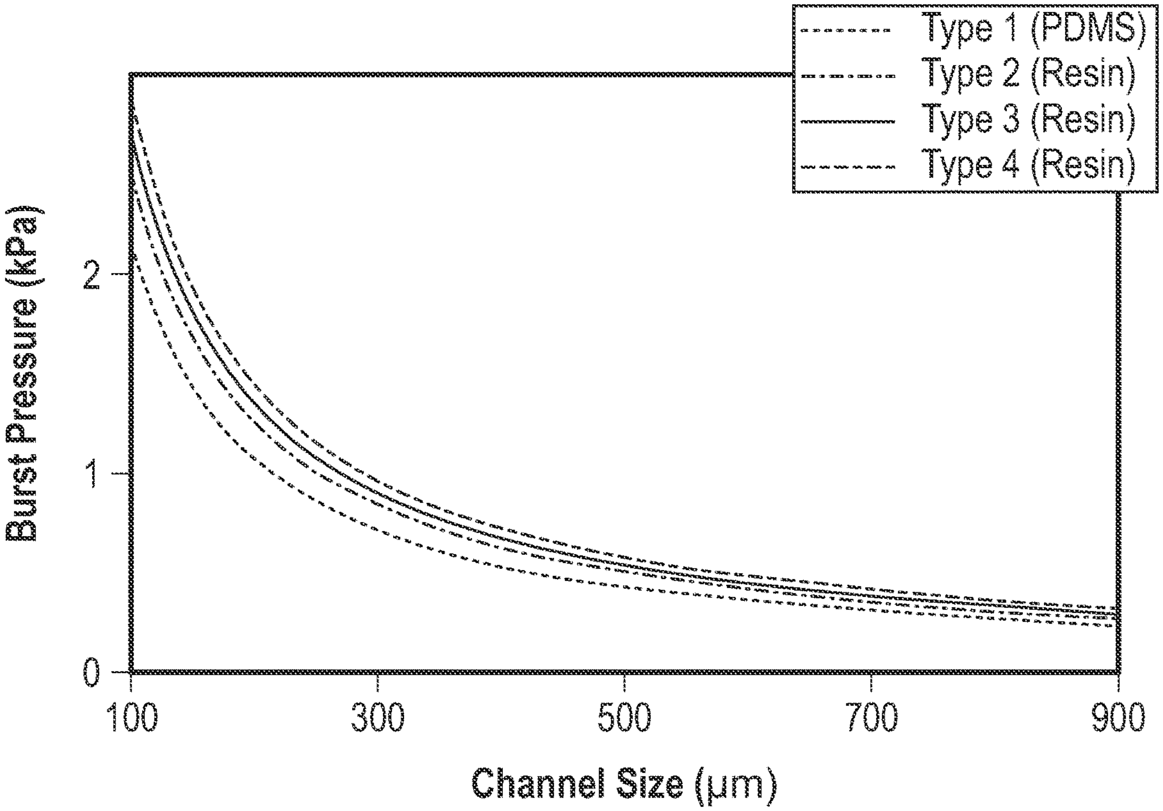
FIG. 13A is a plot of theoretical burst pressure versus channel size for valves according to the CBV designs of FIGS. 12A-12D.

FIG. 13A shows the theoretical BP (calculated from the Young-Laplace equation) versus channel size (square channel) for the four CBV designs of FIGS. 12A-12D with 0.072 N/m (surface tension of water) and θ+=120° (PDMS) for the 2D CBV (Type 1 in FIG. 12A) and θ+=60° for the 3D CBVs (3D printed resin, Types 2-4 in FIGS. 12B-12D). It is shown that BP is inversely proportional to channel size.

Figure 13B:
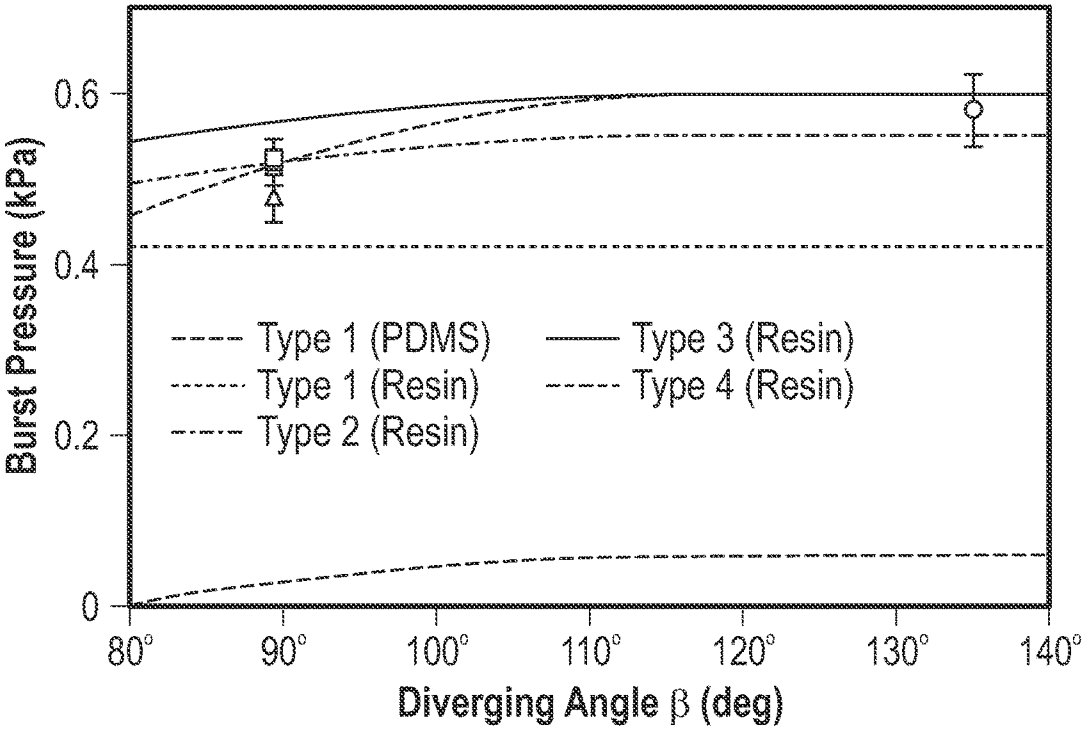
FIG. 13B is a plot of theoretical burst pressure as a function of diverging angle β for valves according to the CBV designs of FIGS. 12A-12D.

FIG. 13B is a plot of theoretical burst pressure as a function of diverging angle β for valves according to the CBV designs of FIGS. 12A-12D, for a channel with a fixed geometry of 600 μm width and 400 μm height. The analytical model reveals that for a given channel size, BP increases for 3D CBV designs (resin) in comparison to a 2D CBV (PDMS). Within the subset of 3D CBV designs, the channel diverging angles (β, γ) dictate the valve BP ($BP_{Type\ 4} > BP_{Type\ 3} > BP_{Type\ 2}$). Different diverging angle designs provide different BP values. The ability to produce numerous different CBVs of different BP values in a single device permits fabrication of complex multi-chamber epifluidic devices with predictable sequential direction of fluid flow therein.

Figure 14A:
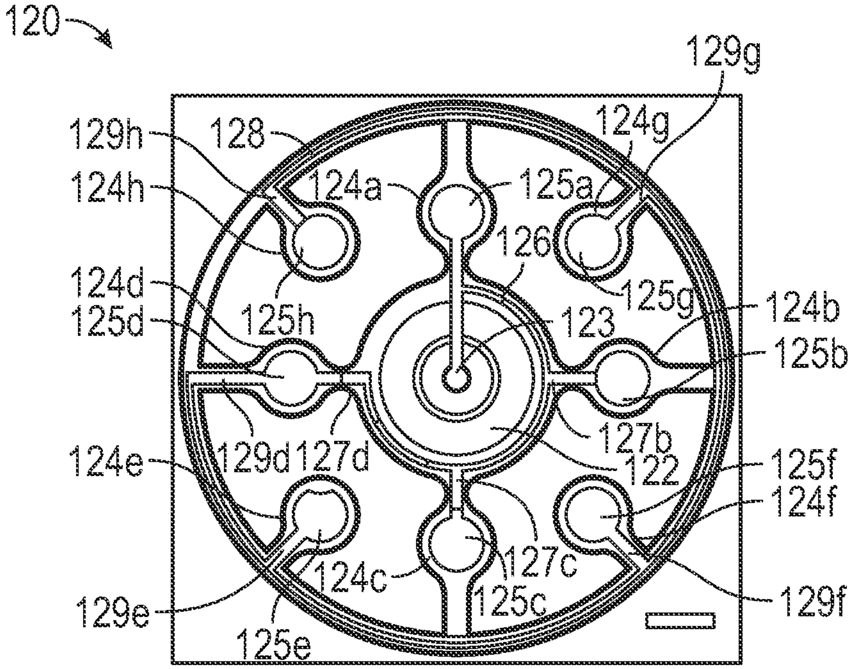
FIG. 14A is a top plan view of at least a portion of an epidermal microfluidic device according to one embodiment, with eight reservoir-defining distal portions arranged around a central portion, and inner and outer connecting channels.

FIG. 14A is a top plan view of at least a portion of a circular epidermal microfluidic device 120 according to one embodiment, with eight distal portions 124A-124H (defining fluidic reservoirs 125A-125H) and a distal connecting channel 128 arranged around a central portion 122 that defines a fluid inlet port 123 and a central connecting channel 126, with numerous different CBVs (127B-127D, 129D-129H) therein. A first fluidic reservoir 125A is in fluidic communication with the central connecting channel 126 without an intervening CBV. Inner CBVs 127B-127D are arranged between the central connecting channel and the second to fourth fluidic reservoirs 125B-125D. One outer CBV 129D is proximate to the fourth fluidic reservoir 125D but receives fluid from the central connecting channel 126. Each remaining outer CBV 129E-129H is arranged between the distal connecting channel 128 and a corresponding fluidic reservoir 125E-125H.

Figure 14B:
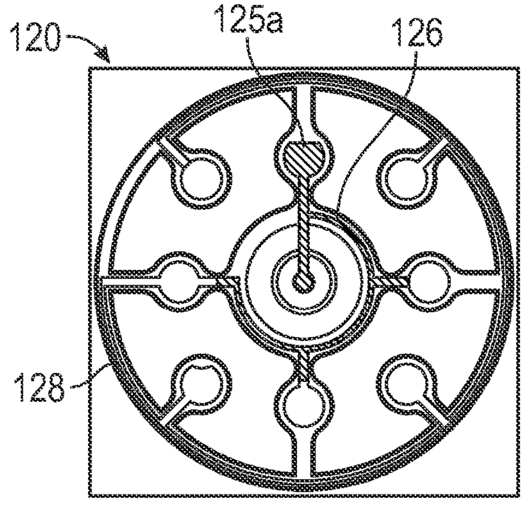
FIGS. 14B-14I illustrate sequential filling of the eight reservoirs of the epidermal microfluidic device of FIG. 14A.
Figure 14C:
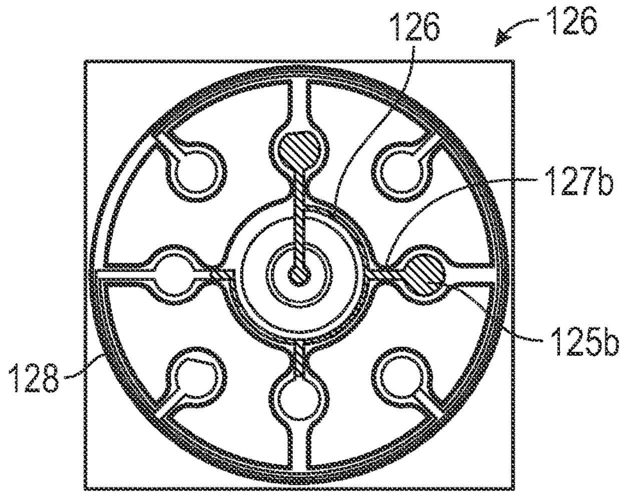
Figure 14D:
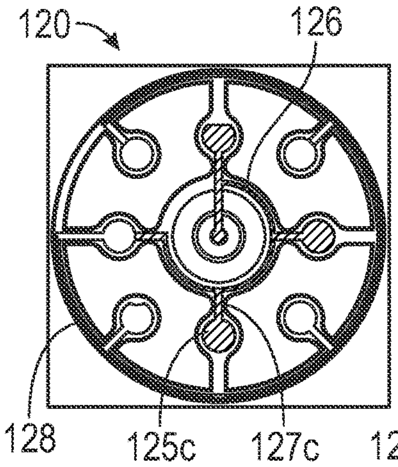
Figure 14E:
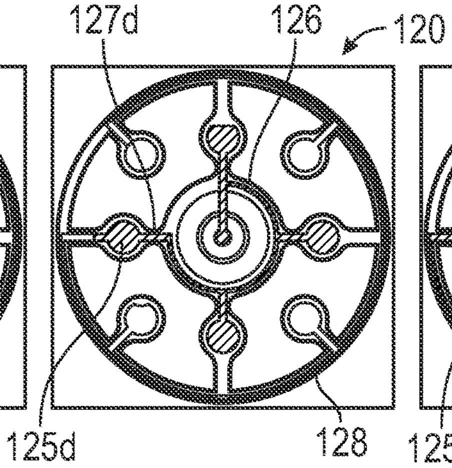
Figure 14F:
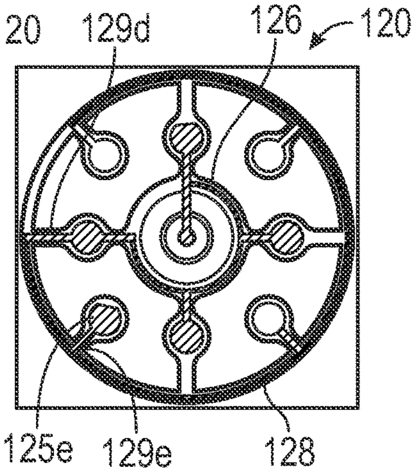
Figure 14G:
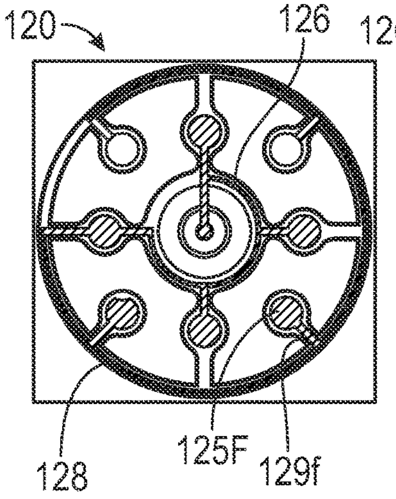
Figure 14H:
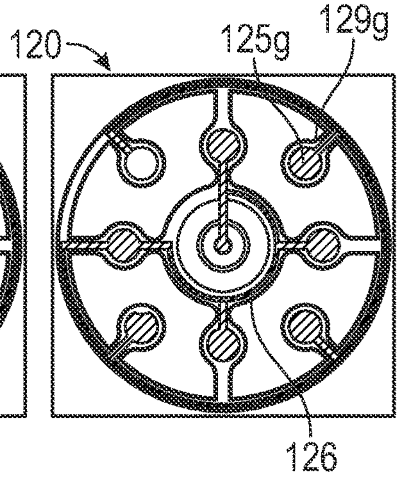
Figure 14I:
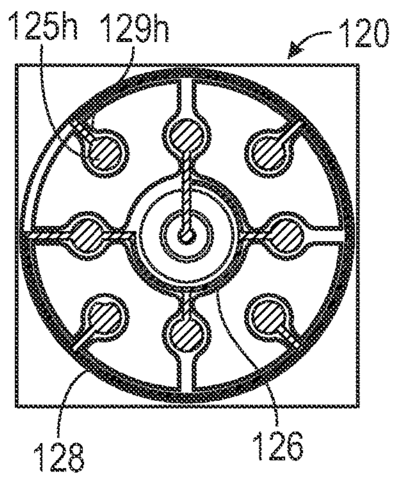

FIGS. 14B-14I illustrate sequential filling of the eight fluidic reservoirs 125A-125H of the epidermal microfluidic device 120 of FIG. 14A. FIG. 14B shows fluid supplied into the central connecting channel 126 and the first fluidic reservoir 125A. FIG. 14C shows fluid supplied through the central connecting channel 126 and an inner CBV 127B into the second fluidic reservoir 125B. FIG. 14D shows fluid supplied through the central connecting channel 126 and an inner CBV 127C into the third fluidic reservoir 125C. FIG. 14E shows fluid supplied through the central connecting channel 126 and an inner CBV 127D into the fourth fluidic reservoir 125D. FIG. 14F shows fluid supplied through the central connecting channel 126 and an outer CBV 129D into the distal connecting channel 128 and an outer CBV 129E into the fifth fluidic reservoir 125E. FIG. 14G shows fluid supplied through the distal connecting channel 128 and an outer CBV 129F into the sixth fluidic reservoir 125F. FIG. 14H shows fluid supplied through the distal connecting channel 128 and an outer CBV 129G into the seventh fluidic reservoir 125G. FIG. 14I shows fluid supplied through the distal connecting channel 128 and an outer CBV 129H into the eighth fluidic reservoir 125H. Design parameters for the CBVs 127E-127D, 129D-129H, identified as Valves 1 to 8, are identified in the following Table 2.

TABLE 2

Design parameters for CBVs

| Valve # | CBV Type | Channel With (μm) | Channel Height (μm) | Theoretical CBV BP (kPa) | Effective Theoretical BP (kPa) |
|---|---|---|---|---|---|
| 1 | N/A | 600 | 600 | N/A | 0.003 |
| 2 | 2 | 600 | 600 | 0.42 | 0.421 |
| 3 | 2 | 500 | 500 | 0.50 | 0.509 |
| 4 | 1 | 200 | 600 | 0.50 | 0.515 |
| 5 | 2 | 500 | 500 | 0.50 | 0.517 |
| 6 | 3 | 500 | 500 | 0.54 | 0.567 |
| 7 | 4 | 500 | 500 | 0.58 | 0.618 |
| 8 | 4 | 400 | 400 | 0.72 | 0.773 |

In addition to CBV design parameters, Table 2 provides theoretical CBV BPs and effective theoretical BPs, which consider the theoretical CBV BP and fluidic resistance of the microfluidic channel network. Imperfections resulting from the 3D-printing process result in experimental burst pressure values below theoretical limits.

Benchtop experiments yield measurements of CBV BPs by means of a positive pressure displacement pump apparatus that perfuses water (dyed blue for visualization) into the microfluidic network at defined pressures. A digital microscope (VHX-7100, Keyence Corp., Japan) produced micrographs of the devices. An optical camera (Canon 90D, Canon EF 100 mm f/2.8 L USM lens) provided video capture capabilities (30 frames per second) for device analysis. Measurement of the CBV burst pressure consisted of a "fill test" in which water (dyed blue for visualization) entered a device until flow stopped at the CBV. A modular, calibrated pressure displacement flow system (Flow EZ, Fluigent, France) controlled the fluid pressure and permitted near-instantaneous stepwise increase in pressure (0.1 mbar interval, 10 s dwell time). Video observation identified the pressure threshold for fluid to burst each CBV.

Figures 15A, 15B, 15C, 15D, 15E, 15F:
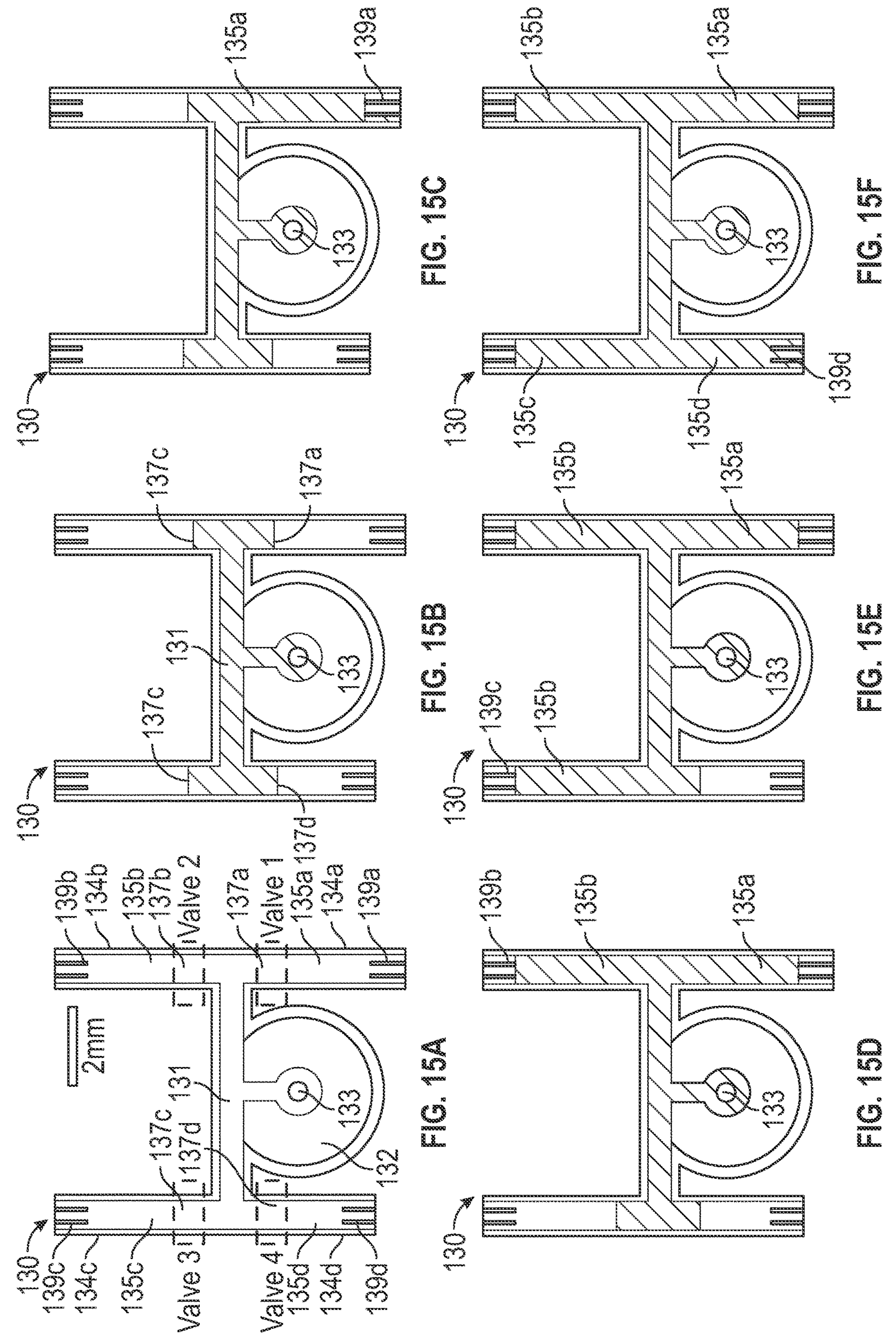
FIG. 15A illustrates an H-shaped epidermal microfluidic device with one central inlet and four capillary burst valves in an empty state.
FIGS. 15B-15F show the device of FIG. 15A in sequential states of being filled with liquid.

FIG. 15A illustrates an H-shaped epidermal microfluidic device 130 with one fluidic inlet port 133, a distribution channel 131, four CBVs 137A-137D, and four fluidic reservoirs 135A-135D defined in four distal portions 134A-134D, with the device 130 in an empty state. The device 130 includes a truncated circular shaped central portion 132 defining the fluidic inlet port 133, wherein the distribution channel 131 crosses the central portion 132 and branches into the four distal portions 134A-134D. Each distal portion 134A-134D has an associated ventilation structure 139A-139D to permit air to exit a fluidic reservoir 135A-135D as it is filled with an advancing front of fluid. The CBVs 137A-137D are configured with different burst pressures to permit the four fluidic reservoirs 135A-135D to be filled in a sequential manner.

FIGS. 15B-15F show the epidermal microfluidic device 130 of FIG. 15A in sequential states of being filled with fluid. FIG. 15B shows the epidermal microfluidic device 130 after fluid is supplied through the fluid inlet port 133 into the distribution channel 131 up to the four CBVs 137A-137D. FIG. 15C shows the epidermal microfluidic device 130 after fluid has flowed through the first CBV 137A (shown in FIG. 15A) into the first fluidic reservoir 135A and air has exhausted through the first ventilation structure 139A. FIG. 15D shows the epidermal microfluidic device 130 after fluid has flowed through the second CBV 137B (shown in FIG. 15A) into the second fluidic reservoir 135B and air has exhausted through the second ventilation structure 139B. FIG. 15E shows the epidermal microfluidic device 130 after fluid has flowed through the third CBV 137C (shown in FIG. 15A) into the third fluidic reservoir 135C and air has exhausted through the third ventilation structure 139C. FIG. 15F shows the epidermal microfluidic device 130 after fluid has flowed through the fourth CBV 137D (shown in FIG. 15A) into the fourth fluidic reservoir 135D and air has exhausted through the fourth ventilation structure 139D.

Figures 16A, 16B, 16C, 16D, 16E:
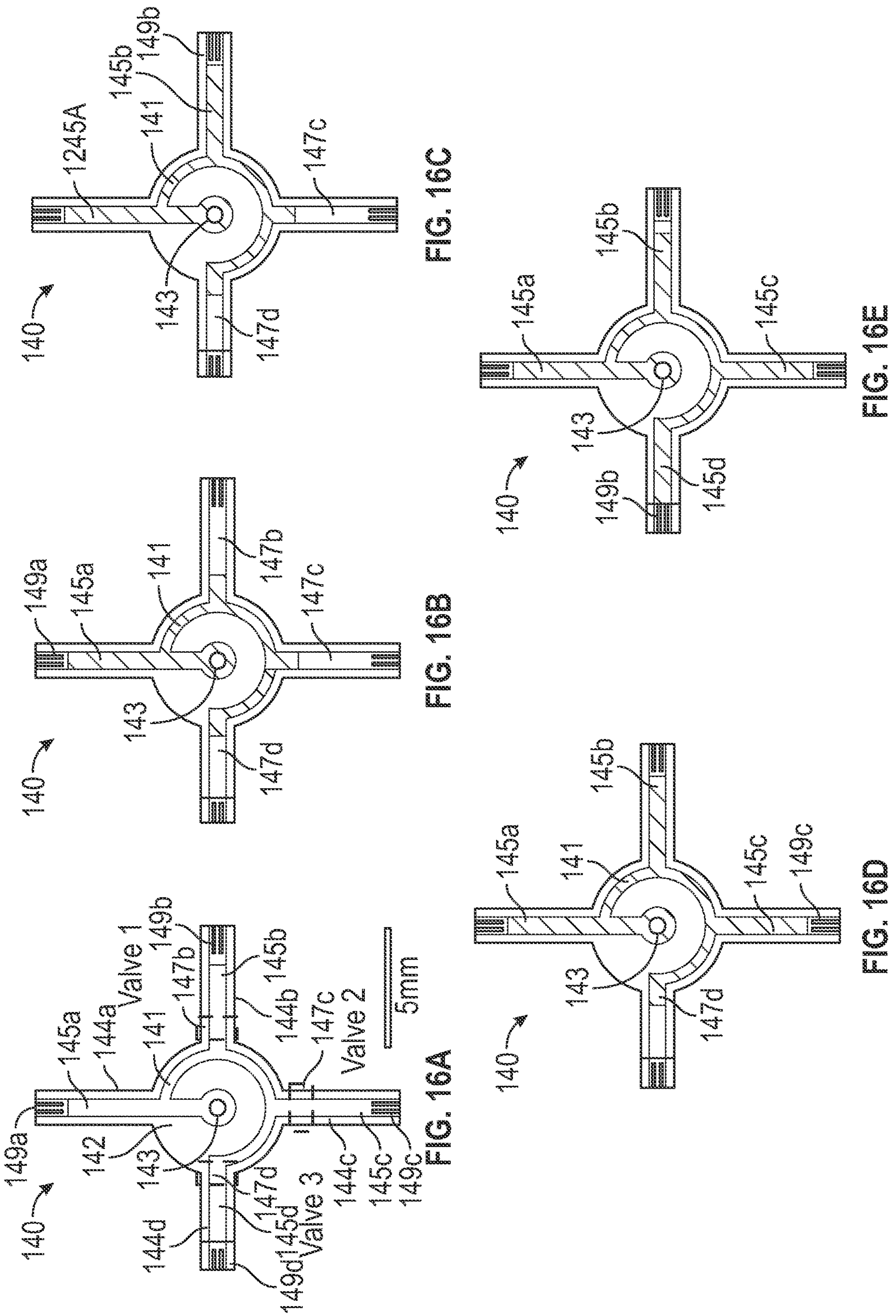
FIG. 16A illustrates a cross-shaped epidermal microfluidic device with one central inlet and three capillary burst valves in an empty state.
FIGS. 16B-16E show the device of FIG. 16A in sequential states of being filled with liquid.

FIG. 16A illustrates a generally cross-shaped epidermal microfluidic device 140 with a fluidic inlet port 143 and a distribution channel 141 defined in a circular central portion 142, and four fluidic reservoirs 145A-145D and three CBVs 147B-147D defined in distal portions 144A-144D, with the device 140 being in an empty state. Each distal portion 144A-144D has an associated ventilation structure 149A-149D to permit air to exit a fluidic reservoir 145A-145D as it is filled with an advancing front of fluid. The CBVs 147B-147D are configured with different burst pressures to permit the second to fourth fluidic reservoirs 145B-145D to be filled in a sequential manner. FIG. 16B shows the epidermal microfluidic device 140 after fluid is supplied through the fluid inlet port 143 into the distribution channel 141 up to the three CBVs 147B-147D, as well as into the first fluidic reservoir 145A (which lacks an associated CBV) as air is exhausted through the first ventilation structure 149A. FIG. 16C shows the epidermal microfluidic device 140 after fluid has flowed through CBV 147B (shown in FIG. 16A) into the second fluidic reservoir 145B as air is exhausted through the second ventilation structure 149B. FIG. 16D shows the epidermal microfluidic device 140 after fluid has flowed through CBV 147C (shown in FIG. 16A) into the third fluidic reservoir 145C as air is exhausted through the third ventilation structure 149C. FIG. 16E shows the epidermal microfluidic device 140 after fluid has flowed through CBV 147D (shown in FIG. 16A) into the fourth fluidic reservoir 145D as air is exhausted through the fourth ventilation structure 149D.

Figure 17A:
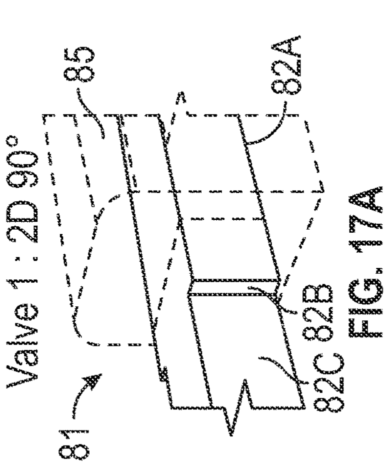
FIGS. 17A-17C schematically illustrate fluid occupying first to third different capillary burst valves, respectively.
Figure 17B:
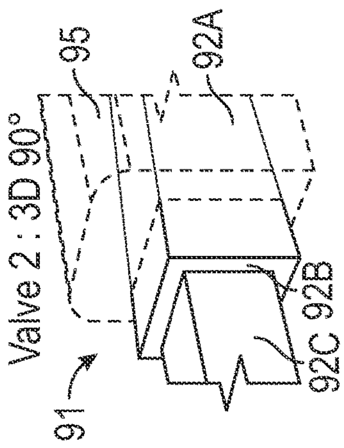
Figure 17C:
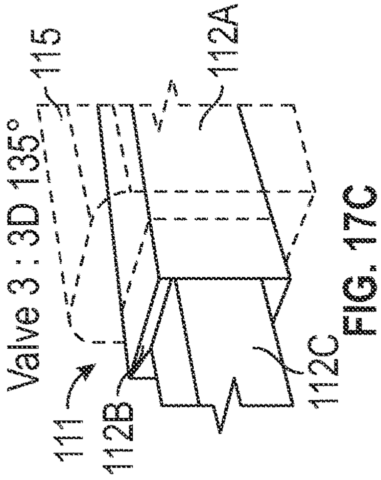
Figure 18A:
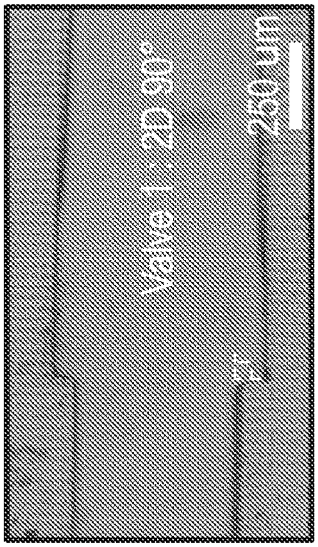
FIGS. 18A-18C are top plan view photographs of capillary burst valves according to the designs of FIGS. 17A-17C, respectively.
Figure 18B:
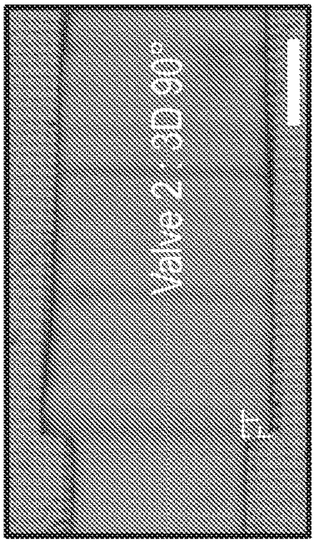
Figure 18C:
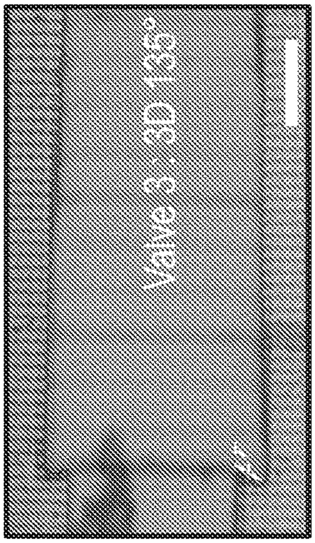
Figure 19A:
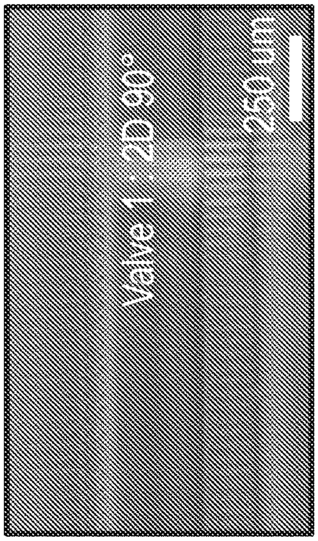
FIGS. 19A-19C are side elevational view photographs of capillary burst valves according to the designs of FIGS. 17A-17C, respectively.
Figure 19B:
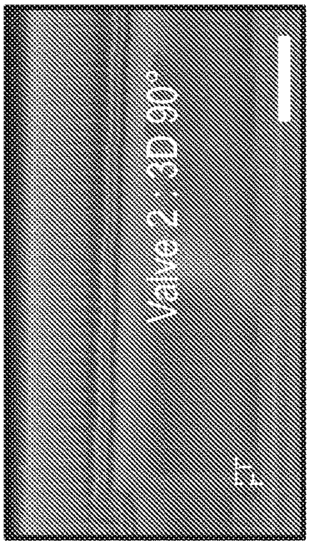
Figure 19C:
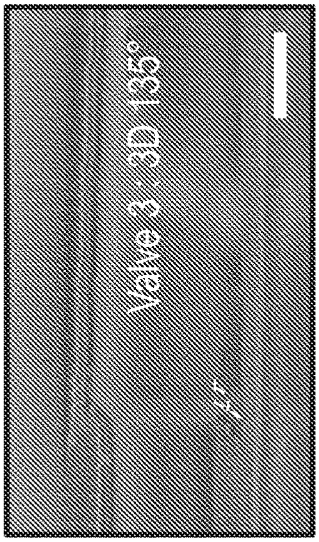

FIGS. 17A-17C show fluid occupying the same CBVs 81, 91, 111 as previously described in FIGS. 12A, 12B, and 12D, respectively, which are reproduced on the same drawing sheet as (i) top plan view photographs of the CBVs 81, 91, 111 in 3D printed microfluidic substrates in FIGS. 18A-18C, respectively, and (ii) side elevational view photographs of these CBVs 81, 91, 111 in 3D printed microfluidic substrates in FIGS. 19A-19C, respectively. The descriptions of CBVs 81, 91, 111 in connection with FIGS. 12A, 12B, and 12D are incorporated by reference. FIGS. 17A, 18A, 19A show a 2D 90 degree CBV 81 with variation in width (with a horizontal diverging angle of 90 degree) but no variation in height. FIGS. 17B, 18B, 19B show a 3D CBV 91 with variations in both height and width, with horizontal and vertical diverging angles of 135 degrees. FIGS. 17C, 18C, 19C show a 3D CBV 111 with variations in both height and width, with horizontal and vertical diverting angles of 135 degrees.

Figure 20A:
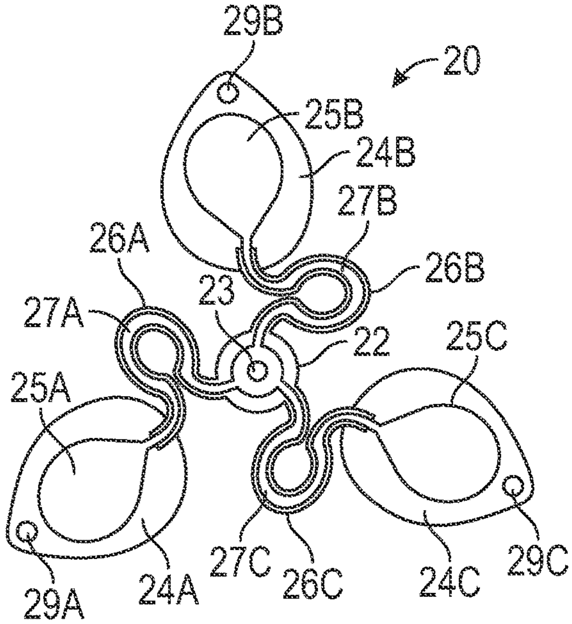
FIGS. 20A-20D illustrate a rigid substrate of an epidermal microfluidic device according to the design of FIG. 1 in four different states of being filled with liquid (i.e., from empty, to first through third reservoirs being filled sequentially).
Figure 20B:
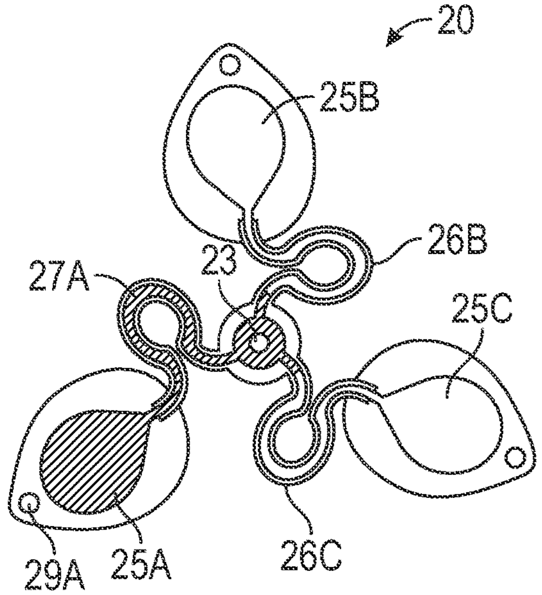
Figure 20C:
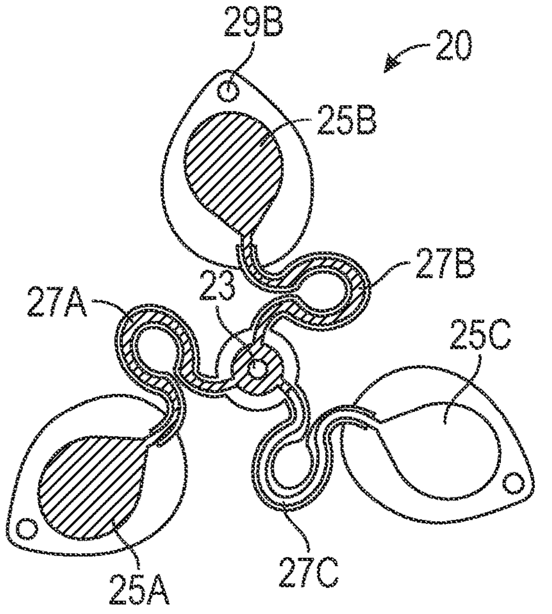
Figure 20D:
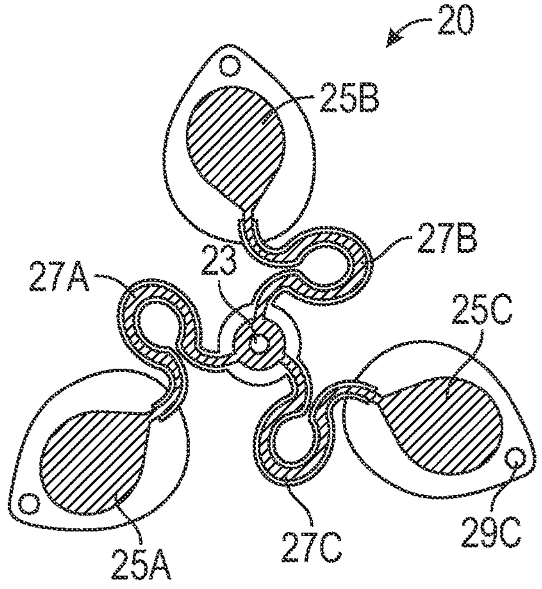

FIGS. 20A-20D illustrate a rigid substrate of an epidermal microfluidic device 20 according to the design of FIG. 1 in four different states of being filled with liquid (i.e., from empty in FIG. 20A, to first through third reservoirs 25A-25C being filled sequentially in FIGS. 20B-20D). The epidermal microfluidic device 20 includes a central portion 22 defining a fluidic inlet port 23, three distal portions 24A-24C defining fluidic reservoirs 25A-25C and having ventilation holes 29A-29C, and linking portions 26A-26C defining microfluidic channels 27A-27C that provide fluid communication between the fluid inlet port 23 and the fluidic reservoirs 25A-25C. FIG. 20B shows fluid being present in the first microfluidic channel 27A and the first fluidic reservoir 25A. FIG. 20C shows fluid being present in the first microfluidic channel 27A and the first fluidic reservoir 25A, and additionally in the second microfluidic channel 27B and the second fluidic reservoir 25B. FIG. 20D shows fluid being present in the first to third microfluidic channels 27A-27C and the first to third reservoirs 25A-25C.

Example—3D Printed Epifluidic Device Fabrication

Each 3D epifluidic device design described herein was created using computer-aided design (CAD) software (AutoCAD 2019, Autodesk, CA, USA). Subsequent export to a stereolithography readable file (.stl) format yielded a file suitable for direct use by the digital light processing (DLP) resin printer (Prime 110, 385 nm, MiiCraft, Taiwan and Creative CADworks, Ontario, Canada). The included printer control software (Utility, v 6.3.0.t3) provided direct control over print parameters for each file including layer height (5 μm to 50 μm), dose, and lamp power. High-fidelity printing was achieved by application of a removable Kapton polyimide tape over the surface of a polished aluminum build plate. The applied tape was free of bubbles and wrinkles to ensure a smooth build surface free of defects.

Devices were printed using transparent resin (MiiCraft BV-007A, Creative CADworks, Ontario, Canada) and a 10 μm layer height (6 devices per build plate, ~20 min total print time). Gentle removal of printed parts from the build plate, soaking in 1% detergent solution (Alconox-1232-1, Alconox, NY, USA) under sonication (CPX2800, Fisher Scientific, PA, USA) for 10 min, drying of device using clean dry air (CDA), post-print UV cure for 10 min (CureZone, MiiCraft, Taiwan), and post-cure bake at 70° C. for 30 min (Model 40E Lab Oven, Quincy Lab Inc., IL, USA) yielded a 3D-printed epifluidic device suitable for direct use or integration with PDMS (e.g., a PDMS epidermal interface layer, optionally in combination with a PDMS reservoir capping layer).

A three-step process facilitated printing fully enclosed 3D-printed devices. Printing epifluidic substrates with open reservoirs (Step 1) and post-print removal of uncured liquid resin by CDA (Step 2) enabled enclosure of the substrates with a thin reservoir capping layer (30 μm) by means of a second print process (Step 3). The printed device remained fixed to the build plate during the "print-pause-print" process to ensure feature alignment. Execution of the above-described post processing steps yielded a fully enclosed epifluidic substrate.

To form PDMS portions (capping layer and epidermal interface layer), liquid PDMS (10:1 base: curing agent, Sylgard 184, Dow Inc., MI, USA) with white pigment (3% w/w, Ignite White, Smooth-On, Inc., PA, USA) was poured onto a sacrificial mylar film (2 mil thickness), spin coated for 30 s (400 rpm for reservoir capping layer; 200 rpm for epidermal interface layer), and cured in an oven (70° C., 2 h) to form films with thicknesses of 200 μm and 400 μm, respectively. A $CO_2$ laser cutter (30 W Epilog Mini 24, Epilog Laser, Colorado, USA) patterned the PDMS films into the final geometries used in the epifluidic devices. A medical-grade adhesive (1524, 3M Inc., MN, USA) patterned in the same manner and bonded to the PDMS interfacial layer, was provided below the epidermal interface layer for bonding to skin of a user.

Hybrid 3D-printed epifluidic devices utilize bonded PDMS capping layers to enclose 3D-printed microfluidic reservoirs. Modification of a previously reported method facilitated a strong bond between PDMS and the printed device. Specifically, rinsing with isopropyl alcohol (2-propanol, A416, Fisher Scientific, Massachusetts, USA), soaking in DI water (Direct-Q 3 UV Water Purification System, MilliporeSigma, Missouri, USA) for 30 min, corona treating with air plasma (BD-20, Electro-Technic, Illinois, USA) for 30 s followed by immediate immersion in a 12% v/v solution of (3-aminopropyl)triethoxysilane (APTES, 440140, MilliporeSigma, MO, USA) for at least 20 min, rinsing in DI water, and drying with CDA prepared the oven-baked 3D-printed substrate for bonding to PDMS. Pipetting colorimetric reagents or flow visualization dye (Soft Gel Paste, AmeriColor Corp., CA, USA) into pre-determined regions occurred prior to sealing of the 3D-printed device substrate. After a 30 s corona treatment, laminating the PDMS capping layer to the APTES-modified printed surface sealed the epifluidic substrate. Heat treating the assembled substrate and PDMS layer on a hotplate (70° C.) under applied weight (3 kg) was performed for 30 min to form a permanent bond. Removal of the sacrificial mylar layer, release from excess PDMS via laser-cutting, and opening the central sweat ingress points using a 1.5 mm diameter circular punch (reusable biopsy punch, World Precision Instruments) yielded a final hybrid epifluidic device.

Example—Method for Sweat Collection Using 3D Printed Epifluidic Devices

A study was performed to evaluate the performance of 3D-printed epifluidic devices (according to the design of FIG. 1) and evaluate the use thereof in collecting and analyzing sweat. Testing involved healthy young adults (N=2, male) as volunteers during normal physical activity (stationary cycling) with no additional human-subject risk.

Cleaning of the forearm of each individual with an alcohol wipe prepared the skin for robust adhesion to an epifluidic device including a 3D printed substrate, a reservoir capping layer, an adhesive gasket, an epidermal interface layer, and a skin-facing adhesive layer. The exercise regime comprised stationary cycling under approximately constant working load for 50 min in a controlled laboratory environment (22° C., 55% RH).

Evaluation of sequential generation of aliquots of sweat required periodic monitoring of the filling of an epifluidic device. Once all reservoirs filled, as determined by visual observation, a first (initially attached) device portion (including a first 3D printed substrate, first reservoir capping layer, and first adhesive gasket) was removed from the epidermal interfacial layer and replaced with a second device portion (including a second 3D printed substrate, second reservoir capping layer, and second adhesive gasket, all being identical to their counterparts in the first device portion) applied to the epidermal interface layer while the volunteer continued to exercise. Evaluation of colorimetric performance of the epifluidic devices required individual subjects to wear two separate epifluidic devices (i.e., one colorimetric and one collection (as a control)), located in close proximity on the same arm. Prior to device removal, a photograph of the colorimetric epifluidic device was recorded at the conclusion of the collection period for image processing and chloride analysis. Extraction of sweat from the individual reservoirs of the collection epifluidic device at the conclusion of the exercise period facilitated chloride measurements using a ChloroChek Chloridometer.

Figure 21A:
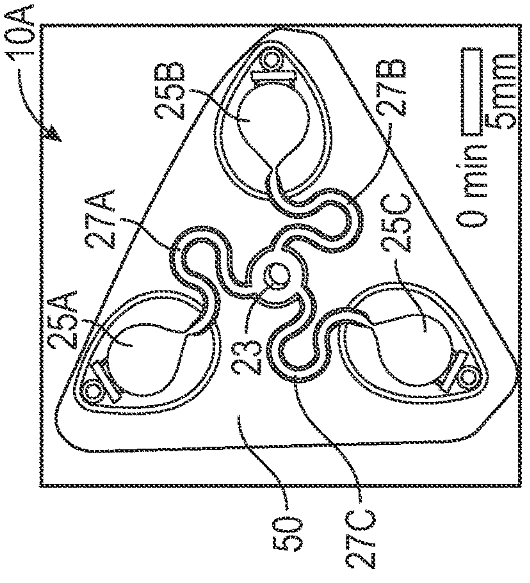
FIGS. 21A-21F show steps in performing sweat collection on a human subject during exercise using epidermal microfluidic devices and an epidermal interface layer, with FIGS. 21A-21D utilizing a first epidermal microfluidic device portion, and with FIGS. 21E-21F utilizing a second epidermal microfluidic device portion.
Figure 21B:
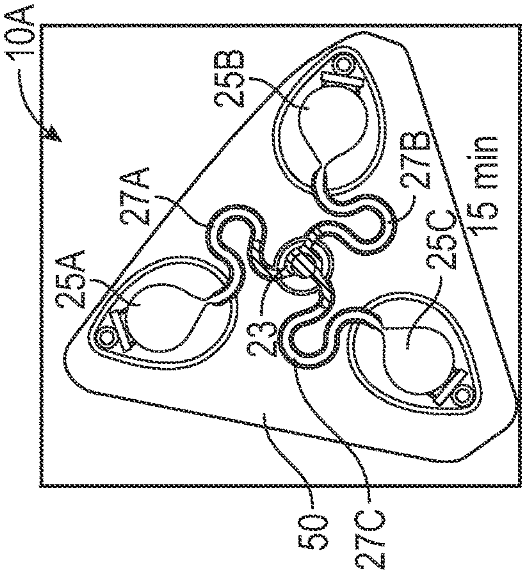
Figure 21C:
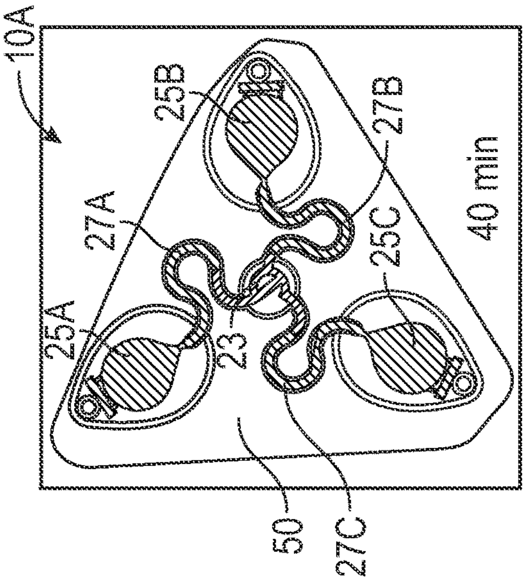
Figure 21D:
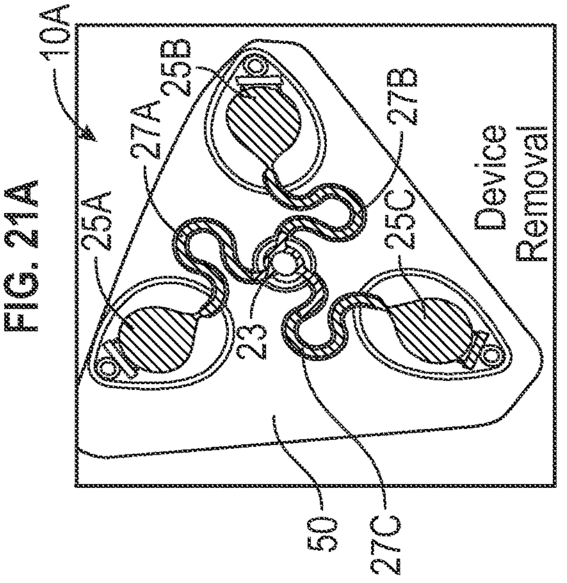
Figure 21E:
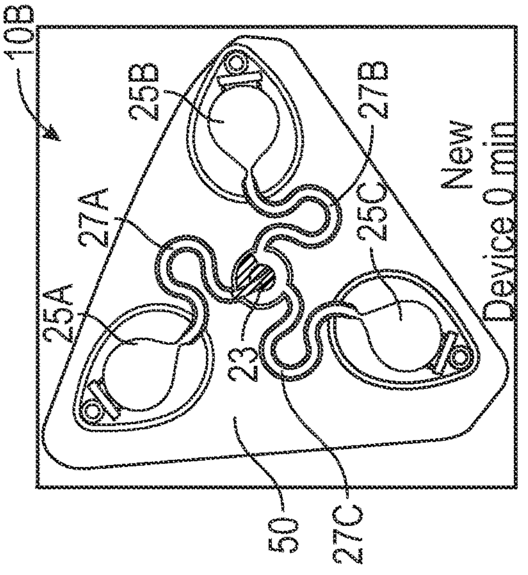
Figure 21F:
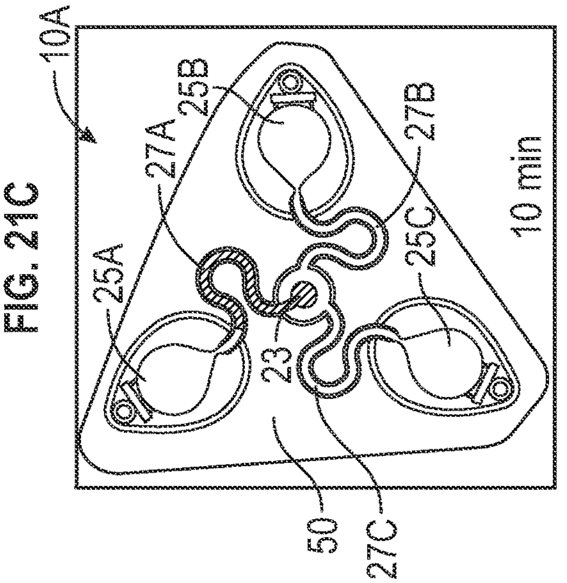

FIGS. 21A-21F show steps in performing sweat collection on a human subject during exercise using epidermal microfluidic devices and an epidermal interface layer, with FIGS. 21A-21D utilizing a first epidermal microfluidic device portion 10A (including a 3D printed substrate, reservoir capping layer, and adhesive gasket according to FIG. 1, the substrate having an inlet port 23 and three fluidic reservoirs 25A-25C) arranged over an epidermal interface layer 50 and underlying adhesive layer (not shown), and with FIGS. 21E-21F utilizing a second epidermal microfluidic device portion 10B (identical to the first device portion 10A) arranged over the same epidermal interface layer 50. FIG. 21A shows the epidermal microfluidic device portion 10A in an unfilled state, at time=0. FIG. 21B shows epidermal microfluidic device portion 10A in a partially filled state at time=15 min, with fluid occupying the fluidic inlet port 23 and portions of channels 27A-27C connecting the fluidic inlet port 23 to the fluidic reservoirs 25A-25C. FIG. 21C shows the epidermal microfluidic device portion 10A in a completely filled state at time=40 min, with fluid from the fluidic inlet port 23 filling the channels 27A-27C and all three fluidic reservoirs 25A-25C. FIG. 21D shows initiation of removal (e.g., by manual peeling) of the device portion 10A from the epidermal interface layer 50, with fluid remaining in the channels 27A-27C and all three fluidic reservoirs 25A-25C. Thereafter, a second epidermal microfluidic device portion 10B (including a 3D printed substrate, reservoir capping layer, and adhesive gasket according to FIG. 1) is provided over the epidermal interface layer 50 to continue collection of sweat from a user undergoing exercise, as shown in FIG. 21E with the second epidermal microfluidic device portion 10B in an unfilled state. With continued sweat collection, FIG. 21F shows the second epidermal microfluidic device portion 10B in a partially filled state, with sweat supplied through fluidic inlet port 23 into first channel 27A.

Figure 22:
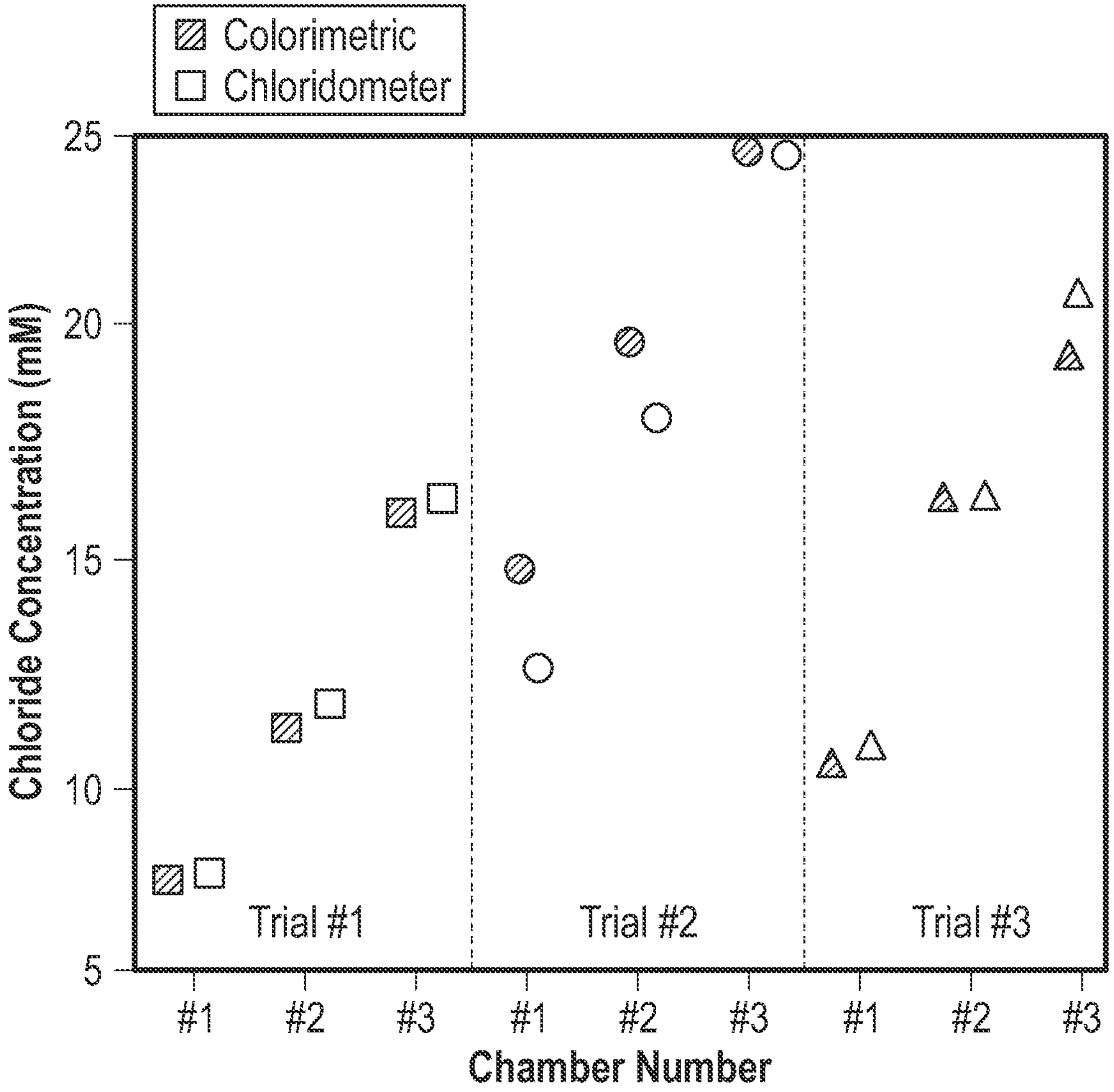
FIG. 22 is a plot showing concentration of sweat chloride from collected sweat measured by chloridometer and colorimetric epidermal microfluidic devices for three different exercise trials.

FIG. 22 is a plot showing concentration of sweat chloride from collected sweat measured by chloridometer and colorimetric epidermal microfluidic devices for three different exercise trials. As shown, chloride concentrations obtained by colorimetric analysis using epidermal microfluidic devices provide results comparable to chloridometer analysis, validating the utility of the colorimetric analysis.

A chloride colorimetric assay solution was produced by thoroughly vortexing 50 mg of silver chloranilate (MP Biomedicals, CA, USA) in 200 μL of a solution of 2% (w/v) polyhydroxyethylmethacrylate (pHEMA, 529265, MilliporeSigma, Missouri, USA) in methanol (A412, Fisher Scientific, Massachusetts, USA) to yield a homogenous suspension. Spotting 2 μL of this solution via laboratory pipette onto the 3D-printed device near the central sweat ingress point, followed by drying in an oven for 30 min prior to encapsulation, prepared the epifluidic device for colorimetric chloride measurements.

To develop standard color and color reference markers, sodium chloride (S271, Fisher Scientific, MA, USA) in DI water was mixed to produce standard test solutions (0, 10, 20, 30, 50, 75, 90, 110, 130, 150 mM), and clinical-grade chloridometer measurements (ChloroChek, ELITech Group, Inc.) yielded validated test solution concentrations. Digital imaging and analysis of sample reservoirs containing one standard solution reacted with the silver chloranilate assay under uniform illumination formed a set of reference images. The sample reservoirs were of the same depth as the epifluidic channels to ensure accurate color representation.

A digital smartphone camera captured images during on-body field tests. A color calibration card (ColorChecker Classic, X-Rite, MI, USA) in the frame of each image facilitated accurate color extraction under various illumination conditions. An open-source photography software package (Darktable 3.0.0, Darktable.org) served as the platform for calibrating images using the color reference card. Analysis of calibrated images using MATLAB (R2019b, The MathWorks Inc., MA, USA) enabled cropping multiple regions of interest from images and extraction of CIELAB color values (L, A, B) for chroma analysis. Mapping of chroma values from colorimetric samples of known reference chloride solutions yielded colorimetric calibration charts with a power-law relationship. The obtained calibration chart supported quantification of the sweat chloride concentration in on-body field testing.

The present disclosure thus provides skin-interfaced wearable systems with integrated microfluidic structures (channel, valve, reservoir) and sensing capabilities (e.g., optical, electrochemical), offering powerful platforms for monitoring the signals arising from natural physiological processes, and providing utility not offered with epifluidic devices having two-dimensional structures produced with flexible substrates.

Those skilled in the art will recognize improvements and modifications to the preferred embodiments of the present disclosure. All such improvements and modifications are considered within the scope of the concepts disclosed herein and the claims that follow. Any of the various features and elements as disclosed herein may be combined with one or more other disclosed features and elements unless indicated to the contrary herein.

The invention claimed is:

1. An epidermal microfluidic device comprising:

a unitary rigid substrate forming a body defining a fluid inlet port, a plurality of fluidic reservoirs, and a plurality of fluidic channels permitting fluidic communication between the fluid inlet port and the plurality of fluidic reservoirs;

an adhesive layer defining a first aperture positionally registered with the fluid inlet port, the adhesive layer being configured to be positioned between the rigid substrate and skin of a user;

an epidermal interface layer comprising a flexible material, configured to be positioned between the adhesive layer and the rigid substrate, and defining a second aperture; and an adhesive gasket configured to be positioned between the epidermal interface layer and the rigid substrate, and defining a third aperture;

wherein the second aperture and the third aperture are positionally registered with the first aperture and the fluid inlet port; and wherein portions of at least some of the fluidic reservoirs and/or at least some of the plurality of fluidic channels comprise gradient variations in height within the rigid substrate.

2. The epidermal microfluidic device of claim 1, wherein the rigid substrate comprises an elastic modulus of at least 500 MPa.

3. The epidermal microfluidic device of claim 1, further comprising a reservoir capping layer arranged between the rigid substrate and the adhesive layer, wherein the reservoir capping layer comprises a fourth aperture positionally registered with the first aperture and the fluid inlet port.

4. The epidermal microfluidic device of claim 1, wherein the adhesive gasket comprises a maximum width that is smaller than a maximum width of the adhesive layer.

5. The epidermal microfluidic device of claim 1, wherein the body of the rigid substrate comprises a plurality of fused dots, rods, or layers.

6. The epidermal microfluidic device of claim 1, wherein the plurality of fluidic channels comprises one or more capillary burst valves that comprise gradient variations in height within the rigid substrate.

7. The epidermal microfluidic device of claim 1, wherein the plurality of fluidic channels comprises one or more capillary burst valves.

* * * * *